United States Patent
Sato et al.

(10) Patent No.: US 7,854,168 B2
(45) Date of Patent: Dec. 21, 2010

(54) THICKNESS MEASURING DEVICE FOR VESSEL STEEL PLATE

(75) Inventors: Nobuyoshi Sato, Zama (JP); Kazuhiro Nojiri, Yokohama (JP); Hiroyuki Haga, Yokohama (JP); Jiro Nakayama, Kitakyusyu (JP); Yuji Nishimura, Kitakyusyu (JP)

(73) Assignee: Asahi Kasei Engineering Corporation, Osaka (JP)

( * ) Notice: Subject to any disclaimer, the term of this patent is extended or adjusted under 35 U.S.C. 154(b) by 63 days.

(21) Appl. No.: 12/285,500

(22) Filed: Oct. 7, 2008

(65) Prior Publication Data

US 2009/0114025 A1     May 7, 2009

Related U.S. Application Data

(62) Division of application No. 10/532,601, filed as application No. PCT/JP03/13631 on Oct. 24, 2003, now Pat. No. 7,513,161.

(30) Foreign Application Priority Data

Oct. 25, 2002    (JP)    ............................. 2002-311288

(51) Int. Cl.
*G01N 29/00*    (2006.01)

(52) U.S. Cl. ............................ 73/622; 73/635; 73/640

(58) Field of Classification Search ........... 73/633–640, 73/618–624, 626–628
See application file for complete search history.

(56) References Cited

U.S. PATENT DOCUMENTS

| 4,010,636 | A | 3/1977 | Clark et al. |
| 4,662,380 | A | 5/1987 | Riley |
| 4,672,852 | A | 6/1987 | Gugel et al. |
| 4,924,707 | A | 5/1990 | Kliesch |
| 5,535,628 | A | 7/1996 | Rutherford |
| 5,571,968 | A | 11/1996 | Buckley |
| 5,619,423 | A | 4/1997 | Scrantz |
| 5,814,731 | A | 9/1998 | Alexander et al. |
| 7,360,427 | B2 | 4/2008 | Drinkwater et al. |
| 7,513,161 | B2 * | 4/2009 | Sato et al. ..................... 73/622 |

FOREIGN PATENT DOCUMENTS

| JP | 53097888 | 8/1978 |
| JP | 56086376 | 7/1981 |
| JP | 60069507 | 4/1985 |
| JP | 60058505 | 8/1985 |

(Continued)

*Primary Examiner*—Helen C. Kwok
(74) *Attorney, Agent, or Firm*—Finnegan, Henderson, Farabow, Garrett & Dunner, L.L.P.

(57) ABSTRACT

The invention is objected to enable the provision of an vessel steel plate measuring device capable of measuring the thickness of vessel steel plate, even in the case of a vessel having a vessel mirror part formed by a spherical or conical curved surface such as a reactor (reaction vessel) and various kinds of obstructions at a vessel barrel. The structure of the device is characterized in that a supporting point member 20 is detachably provided from a supporting point set at the central axis of the vessel mirror part 1a of a reactor 1, and a traveling carrier 6 traveling on a steel plate of the vessel mirror part 1a and having plural ultrasonic probes 7 mounted thereon is connected to one end of a turning radius regulating member 19 rotatively provided around the supporting point member 20.

2 Claims, 36 Drawing Sheets

FOREIGN PATENT DOCUMENTS

| | | |
|---|---|---|
| JP | 62117534 (A) | 5/1987 |
| JP | 62129170 | 6/1987 |
| JP | 63079059 | 4/1988 |
| JP | 1209360 | 8/1989 |
| JP | 1235887 | 9/1989 |
| JP | 4297244 | 10/1992 |
| JP | 11023246 | 1/1999 |
| JP | 2000292142 | 10/2000 |
| JP | 2001082949 | 3/2001 |
| JP | 2001188009 | 7/2001 |
| JP | 2002115491 | 4/2002 |
| JP | 2002228575 | 8/2002 |

* cited by examiner

FIG 6
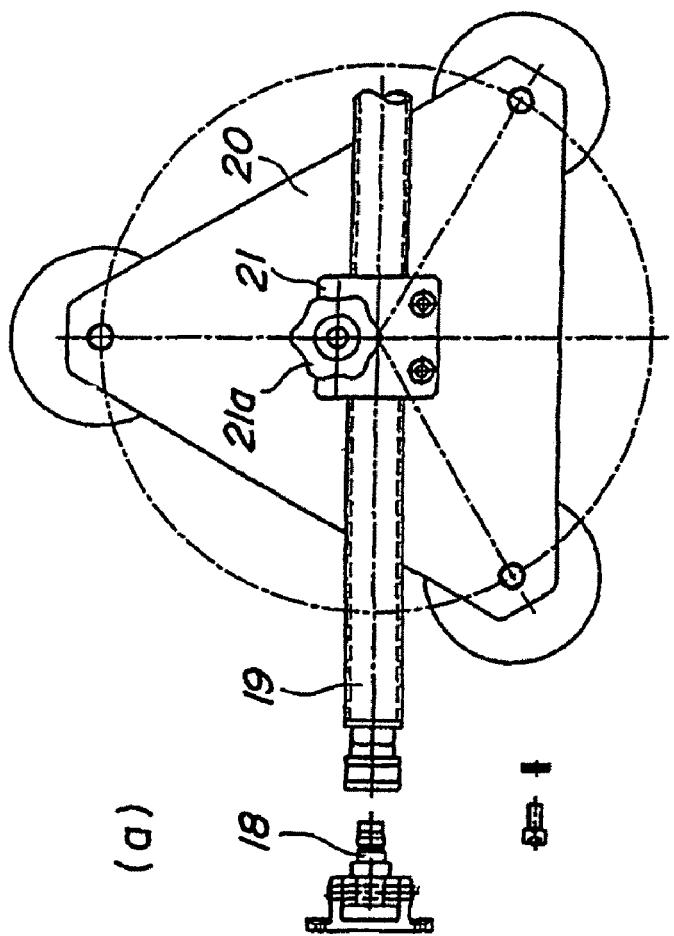
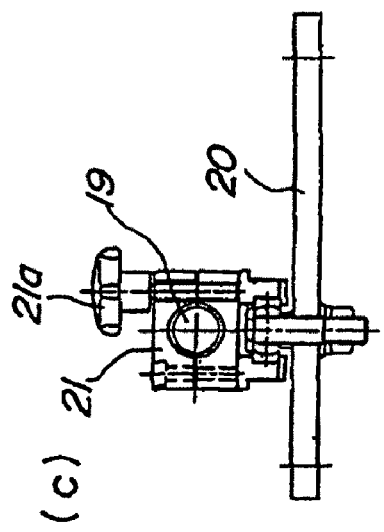
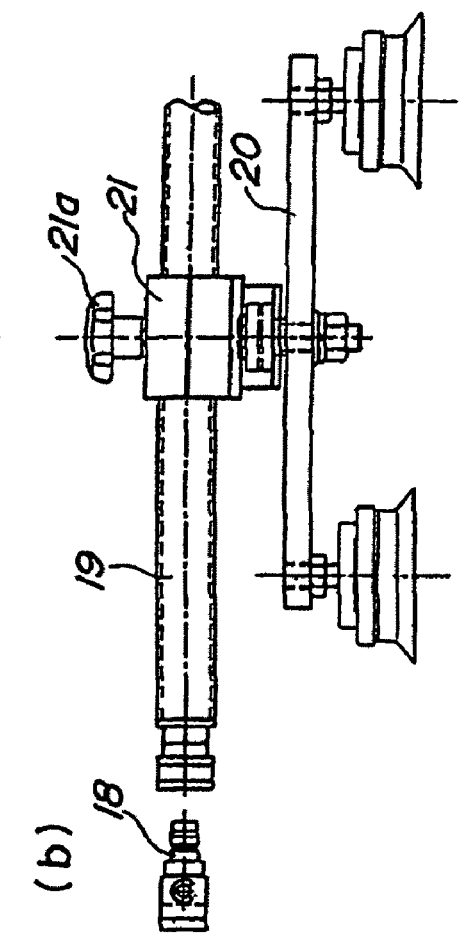

FIG.22
(a)
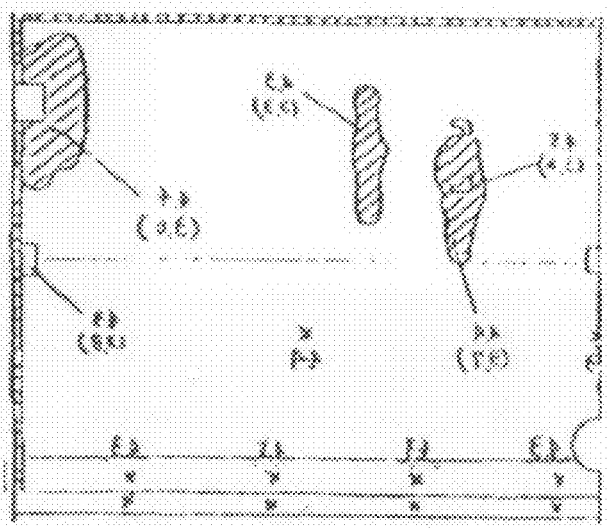
(b)
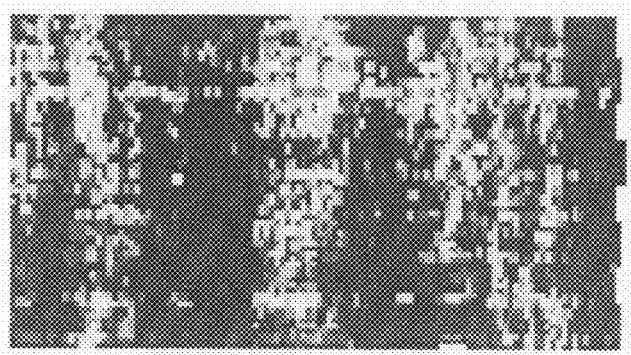
(c)

FIG.28
(a)
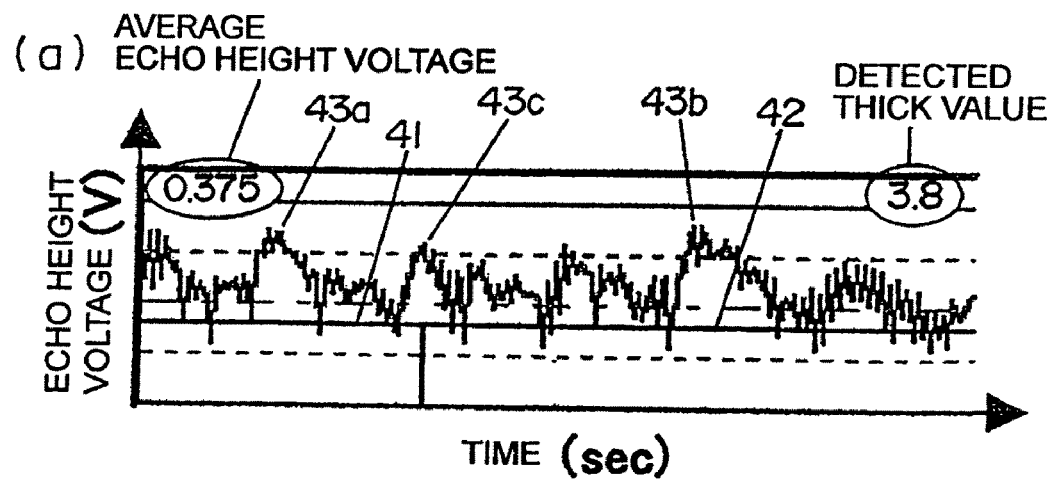
(b)
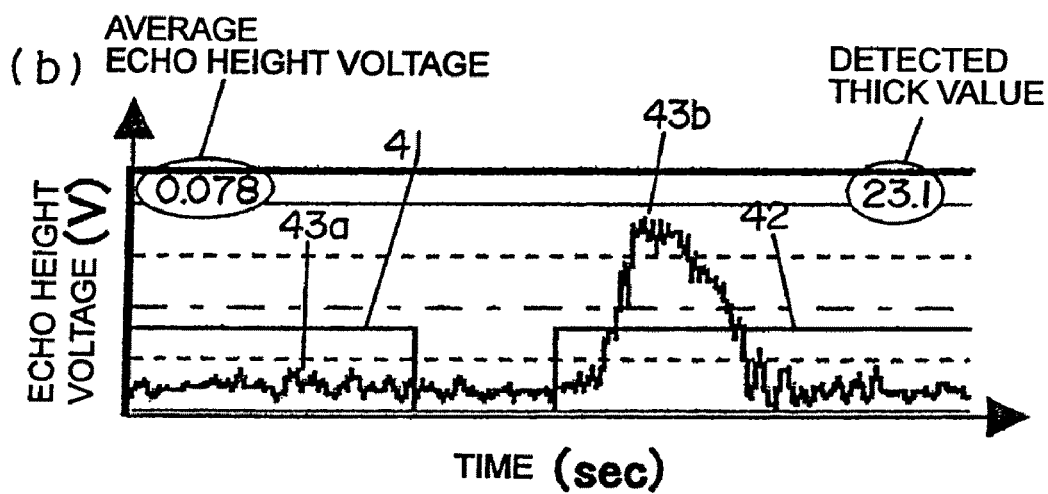
(c)
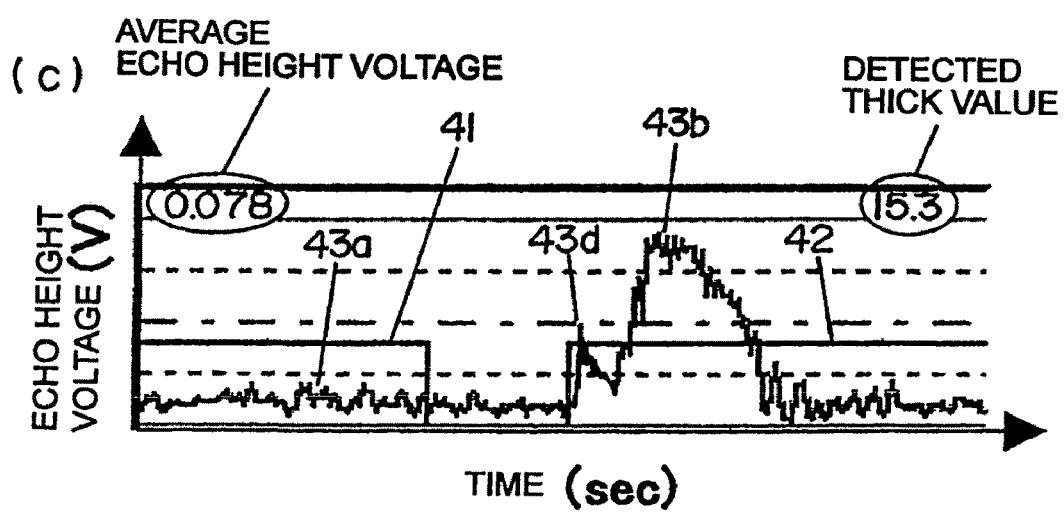

US 7,854,168 B2

THICKNESS MEASURING DEVICE FOR VESSEL STEEL PLATE

RELATED APPLICATION

This application is a divisional of U.S. application Ser. No. 10/532,601 filed Dec. 28, 2005, now U.S. Pat. No. 7,513,161, which is a §371 of International Application No. PCT/JP2003/013631 filed Oct. 24, 2003, which claims priority of Japanese Application No. 2002-311288 filed Oct. 25, 2002, the contents of all of which are incorporated herein by reference.

TECHNICAL FIELD

The present invention relates to a device for measuring the thickness of vessel steel plate, and specifically, a thickness measuring device and a thickness measuring method capable of measuring the thickness of vessel steel plate in the case of a vessel having a vessel mirror part (vessel bottom) formed by a spherical or conical curved surface such as a reactor (reaction vessel) and obstructions such as a baffle and agitating member at a vessel barrel, a noise determining method, and further, a repaired portion designating method.

BACKGROUND ART

Conventionally, in welded steel structures such as tower tanks, spherical tanks, baths, vessels (hereinafter, simply referred to as "vessels"), since aged deterioration due to exterior corrosion occurs, detection and repair by regular thickness measurement have been required.

As means for measuring the thickness of vessel steel plate, the measurement of the thickness of vessel steel plate has been performed by an ultrasonic probe. For example, in order to measure the thickness of flat bottom plate of a cylindrical tank, means for arranging ultrasonic probes and eddy current sensors are arranged in a staggered manner (alternately) on a traveling carriage, and a continuously measuring a steel plate thickness of the tank bottom plate flat surface by traveling the traveling carriage on a coating over the bottom plate surface of the cylindrical tank (see patent document 1) is proposed.

In addition, means for arranging ultrasonic probes in a staggered manner (see patent document 2), means for arranging ultrasonic probes along a width direction and performing thickness measurement of the tank bottom plate via a universal joint mechanism (see patent document 3), and means for supporting ultrasonic probes on a lifting mechanism via a gimbal joint (see patent document 4) are proposed.

Further, in order to measure a side plate curved surface of a floating roof tank, there is means for providing a guide traveling in a horizontal direction near the top of the tank side surface and bottom, connecting a measuring carriage on which ultrasonic probes and permanent magnets for absorption are mounted to a magnet wire rope, and lifting and lowering it by a cable take-up device (see patent document 5).

Further, various kinds of technologies such as means for arranging a traveling carriage on which ultrasonic probes are mounted to be movable vertically and horizontally (see patent document 6), and means for arranging ultrasonic probes to be movable in X-Y direction (see patent document 7) are proposed.

Patent Document 1
  Japanese Patent Application Laid-Open (JP-A) No. 2001-50736

Patent Document 2
  JP-A No. 2-194355

Patent Document 3
  U.S. Pat. No. 5,440,929

Patent Document 4
  JP-A No. 5-26654

Patent Document 5
  JP-A No. 8-304062

Patent Document 6
  JP-A No. 6-347250

Patent Document 7
  JP-A No. 11-19890

In the case of a flat bottom plate of a large size tank simply intended for accommodation of contents or a vessel barrel at which no obstruction exists, effective thickness measurement is possible by the above described various conventional examples, however, in the case of a pressure vessel such as a reactor (reaction vessel), because the vessel is smaller compared to the large size tank simply intended for accommodation of contents, and further, there are many obstructions such as an agitator, agitating blades, a baffle as a filing pipe also serving for accelerating agitation, a gas suction pipe, and a thermometer within the vessel, and the vessel mirror part is formed by a spherical or conical curved surface, automatic entire thickness measurement using an ultrasonic flaw detector has been difficult, and visual detection from the outer surface side of the reactor has been generally performed.

Further, depending on the reactor, sometimes a jacket steel material for circulating hot water or water is provided around the outer circumference of a shell main body for the purpose of heat retaining or temperature adjustment of reaction temperature. While the part between the jacket steel material and the shell main body is exposed to a corrosive environment by the water environment, the outer surface of the shell main body at the part where the jacket steel material has been provided is covered by the jacket steel material. Accordingly, there are problems that the visual detection is difficult from the outer surface side of the shell main body, and a vast amount of cost is needed for once removing the jacket steel material and performing the visual detection, and restoring the jacket steel material again.

In this case, it is conceivable that, once the obstacle within the reactor is removed according to need, temporary scaffolding is provided within the reactor, and the thickness of vessel steel is measured manually using the ultrasonic flaw detector, however, if once the obstacle within the reactor is removed, the work on restoration is complicated and the work on providing and removing the temporary scaffolding is troublesome.

Further, in the case where the thickness of vessel steel is measured in a partial range manually using the ultrasonic flaw detector with the obstruction left within the reactor, because an inspector must perform thickness measurement in tight space in an unstable position, the working environment is bad, and because it takes a long time to measure the thickness of the entire surface of vessel steel without omission, the case is impractical for vessel operation. Accordingly, the thickness has been measured at representative parts of the vessel.

However, since reliability is poor in grasping a state of reduced thickness of the entire vessel only by measuring the thickness at representative parts of the vessel, sometimes the jacket steel material is once removed and the visual detection is performed from the outer surface side of the shell main body as described above.

On the other hand, in a multichannel thickness measuring device using plural ultrasonic probes, as shown in FIG. 23, a range to which intended reflection echoes return is assumed in advance and a boundary surface echo monitoring gate 41 and a bottom surface echo monitoring gate 42 are fixed, thickness values calculated in position where the threshold level of the bottom surface echo monitoring gate 42 cuts the reflection echo waveforms are used as measurement results.

However, in the multichannel thickness measuring device using ultrasonic probes, such a thickness measuring method can not deal flexibly with changes in damaged conditions of measurement surfaces of the independent channels and an object to be inspected, and problems such that accurate thickness values are overlooked and unnecessary noise is erroneously detected occur and those cause great errors in thickness measurement.

For example, in 1 ch (channel) to 4 ch in FIG. 23, thickness values can be accurately detected because the starting time point of the bottom surface echo monitoring gate 42 and the rising time points of bottom surface echo waveforms 43b are substantially matched, however, in other channels, since the thicknesses are calculated in the positions where the bottom surface echo monitoring gate 42 cuts the bottom surface echo waveforms 43b at the falling parts thereof, the thickness values thicker than the real values are detected. Therefore, it is an example in which thin thickness can not be measured and overlooked.

In order to deal with variations in measurement among many channels, as shown in FIG. 24, the conventional fixed gate system can deal with them by broadening the monitoring range of the bottom surface echo monitoring gate 42, however, in this case, there is a disadvantage that unnecessary noise becomes easier to be detected.

For example, in FIG. 24, since the thickness is calculated in the position where the bottom surface echo monitoring gate 42 that has dealt with the variation by broadening the monitoring range cuts a multiple echo waveform 43c in mistake for the bottom surface echo waveform 43b, thickness values thinner than the real values are detected.

Further, in the case where a vessel steel is formed by bonding different materials such as clad steel (e.g., SUS+SS material) and a steel material coated with glass lining (GL+SS material), if a separation (air layer) is produced at the respective boundaries, accurate entire thickness of the target material becomes difficult to be obtained and the separation causes great errors.

FIG. 28(a) shows a boundary surface echo waveform 43a in the case there is a separation at the boundary surface between the surface layer of a vessel steel plate formed by bonding surface layers of different materials and the vessel steel plate. If there is separation in the path of ultrasonic wave, since the multiple echo waveform 43c that is reflected and returned from the separation surface at plural times enters the gate range of the bottom surface echo monitoring gate 42, and the thickness is calculated in the positions where the bottom surface echo monitoring gate 42 cuts the multiple echo waveform 43c, the thickness values thinner than the real values are detected.

Further, in the case where inclusions and lamination exist in the steel material of the vessel steel, since, before the bottom surface echo waveform 43b appears, a flaw echo waveform 43d thereof emerges as shown in FIG. 28(c), the bottom surface echo monitoring gate 42 generally detects flaw echo waveform 43d instead of the bottom surface echo waveform 43b and greatly thinner thickness than the real steel plate thickness is detected as shown by 8 ch (channel) in FIG. 31. Accordingly, there is a problem that, with respect to the steel material with no corrosion, a thin thickness value 44 as if it is corroded is calculated and displayed, and the corrosive reduction of thickness of vessel steel and existence of inclusions etc. can not be discriminated.

Further, in a vessel provided with a jacket steel material on the outer circumference, even when the steel plate thickness is measured from inside using ultrasonic probes, the positions can not be located easily from outside, and, it is necessary to roughly locate the position required for repairing from the outer side from thickness information that has been measured at the inner side, and repair the broad range around the located position. Thereby, there has been a problem that the vessel strength becomes deteriorated by greatly removing the jacket steel material, and time and cost are required for repairing in the broad range.

DISCLOSURE OF THE INVENTION

The invention is to solve the above described problems, and an object thereof is to provide a thickness measuring device and a thickness measuring method, a noise determining method, and further, a repaired portion designating method capable of measuring the thickness of vessel steel plate even in the case of a vessel having a vessel mirror part formed by a spherical or conical curved surface such as a reactor (reaction vessel) and various obstructions at a vessel barrel, capable of easily determining and removing various noises, and further, capable of easily designating portions to be repaired.

A thickness measuring device of vessel steel plate according to the invention for achieving the objects is a device for measuring a thickness of a vessel steel plate characterized by including: a traveling carriage having a steering mechanism that can change a radius of curvature of traveling track and traveling on a steel plate of a vessel mirror part formed by a curved surface having a predetermined curvature and a circular projection form and having a plurality of ultrasonic probes mounted thereon; a supporting point member detachable from a supporting point set at a central axis of the vessel mirror part; and a turning radius regulating member having one end to which the traveling carriage is connected and the other end provided relative to the supporting point member rotatively around the supporting point member, and regulating a spaced distance between the supporting point set at the central axis of the vessel mirror part and the traveling carriage.

Since the invention is arranged as described above, when the steel plate thickness of the vessel mirror part formed by a spherical or conical curved surface having a predetermine curvature and a circular projection form is measured, the steel plate thickness of the vessel mirror part around a lap of the radius of curvature can be measured by mounting the supporting point member to the supporting point set at the central axis of the vessel mirror part, and traveling the traveling carriage on the circumference with a predetermined radius of curvature while regulating the traveling radius of the traveling carriage on which plural ultrasonic probes are mounted by the turning radius regulating member, and the steel plate thickness can be measured substantially over the entire surface of the vessel mirror part by continuously increasing or decreasing the spaced distance between the traveling carriage and the supporting point set at the central axis of the vessel mirror part by the turning radius regulating member with respect to each lap. The supporting point member can be arranged easily detachable from the vessel mirror part because of an attraction force by a magnetic material such as a permanent magnet and electromagnet, or attraction force by a sucker or the like.

Further, another structure of the thickness measuring device of vessel steel plate according to the invention is a device for measuring a thickness of a vessel steel plate characterized by including: a first traveling carriage having a steering mechanism that can change a radius of curvature of traveling track, and capable of traveling on a steel plate of a vessel mirror part formed by a curved surface having a predetermined curvature and a circular projection form; a second traveling carriage having a magnetic material mounted thereon for exerting an attraction force on the vessel steel plate and a traveling driving mechanism that can move left and right of the carriage forward/backward independently, and capable of traveling on a steel plate of a vessel barrel part substantially in a cylindrical form that continues in a direction substantially perpendicular to the vessel mirror part; and an ultrasonic probe unit on which a plurality of ultrasonic probes are mounted, and the device having attaching and detaching means for selectively attaching the ultrasonic probe unit to or detaching the unit from the first traveling carriage and the second traveling carriage.

According to the above structure, by the attaching and detaching means, the common ultrasonic probe unit on which plural ultrasonic probes are mounted can be used by being selectively attached to or detached from the first traveling carriage capable of traveling on the steel plate of the vessel mirror part formed by a curved surface having a predetermined curvature and a circular projection form and the second traveling carriage capable of traveling on the steel plate of the vessel barrel part substantially in a cylindrical form that continues in the direction substantially perpendicular to the vessel mirror part.

The first traveling carriage has the steering mechanism that can change the radius of curvature of traveling track, and the steel plate thickness of the vessel mirror part around a lap of the radius of curvature can be measured by traveling it on the circumference with a predetermined radius of curvature. The steel plate thickness can be measured substantially over the entire surface of the vessel mirror part by continuously increasing or decreasing the radius of curvature of the traveling track with respect to each lap by the steering mechanism.

The second traveling carriage has the magnetic material for exerting an attraction force on the vessel steel plate mounted thereon, and exerts an attraction force to attract the steel plate of the vessel barrel part substantially in a cylindrical form that continues in the direction substantially perpendicular to the vessel mirror part, and thereby, it can stably travel on the steel plate of the vessel barrel part disposed substantially along the vertical direction.

Further, the second traveling carriage has the traveling driving mechanism that can move left and right of the carriage forward/backward independently, and can easily avoid obstructions by turning with a small radius, and the steel plate thickness of the vessel barrel part can be continuously measured by traveling it on the steel plate of the vessel barrel part in the circumference direction or perpendicular (linear) direction.

In the case where there are many obstructions such as an agitator, agitating blades, a baffle as a filing pipe also serving for accelerating agitation, a gas suction pipe, and a thermometer within at the vessel barrel part, the steel plate thickness substantially over the entire surface of the vessel barrel part can be measured by independently moving the left and right part of the second traveling carriage forward/backward by the traveling driving mechanism, and traveling it so as to avoid the obstructions.

Further, another structure of the thickness measuring device of vessel steel plate according to the invention is a device for measuring a thickness of a vessel steel plate characterized by including: a traveling carriage traveling on a vessel steel plate; a carriage member movable relative to the traveling carriage in a direction crossed to a traveling direction of the traveling carriage; a plurality of ultrasonic probes mounted on the carriage member; and obstruction detecting means for detecting obstructions in the traveling direction of the traveling carriage.

According to the above structure, obstructions in the traveling direction of the traveling carriage are detected by the obstruction detecting means, and the runaway and fall of the traveling carriage can be prevented by controlling the traveling driving mechanism of the traveling carriage based on the obstruction detection information. Further, the existence of obstruction can be informed by informing means such as an alarm or an LED (light emitting diode) based on the obstruction detection information.

Further, a thickness measuring method of vessel steel plate according to the invention is a method of continuously measuring thicknesses of a vessel steel plate by detecting echo height voltage values of an ultrasonic response waveform using ultrasonic probes, and the method is characterized by setting a boundary surface echo monitoring gate for detecting echo height voltage values of the ultrasonic response waveform by the ultrasonic probes at the bottom surface of the vessel steel plate in a predetermined duration range, comparing a first thickness of the vessel steel plate calculated in a position where, assuming that the starting time point of the bottom surface echo monitoring gate is the first starting time point, the bottom surface echo monitoring gate cuts the ultrasonic response waveform and a second thickness of the vessel steel plate calculated in a position where, when the starting time point of the bottom surface echo monitoring gate is moved to a second starting time point that is predetermined time earlier than the first starting time point, the bottom surface echo monitoring gate cuts the ultrasonic response waveform, and moving the starting time point of the bottom surface echo monitoring gate to a response time that is predetermined time earlier as long as the second thickness is smaller than the first thickness, and, when the second thickness and the first thickness are equal, fixing the starting time point of the bottom surface echo monitoring gate.

According to the above thickness measuring method, the starting time point of the bottom surface echo monitoring gate can be approximated to the rising time point of the ultrasonic response waveform by the ultrasonic probes at the bottom surface of the vessel steel plate by comparing the first thickness of the vessel steel plate calculated in the position where, assuming that the starting time point of the bottom surface echo monitoring gate is the first starting time point, the bottom surface echo monitoring gate cuts the ultrasonic response waveform and the second thickness of the vessel steel plate calculated in the position where, when the starting time point of the bottom surface echo monitoring gate is moved to a second starting time point that is predetermined time earlier than the first starting time point, the bottom surface echo monitoring gate cuts the ultrasonic response waveform, and moving the starting time point of the bottom surface echo monitoring gate to a response time that is predetermined time earlier as long as the second thickness is smaller than the first thickness, and, when the second thickness and the first thickness are equal, the thickness of the vessel steel plate calculated in the point where the bottom surface echo monitoring gate cuts the ultrasonic response waveform can be measured by fixing the starting time point of the bottom surface echo monitoring gate.

Further, a noise determining method according to the invention is a noise determining method in the case where thicknesses of a vessel steel plate formed by bonding surface layers made of different materials are continuously measured by detecting echo height voltage values of an ultrasonic response waveform using ultrasonic probes from the surface layer side of the vessel steel plate, and the method is characterized by setting a boundary surface echo monitoring gate for detecting echo height voltage values of the ultrasonic response waveform by the ultrasonic probes at a boundary surface between the surface layer and the vessel steel plate in a predetermined duration range, creating a statistical distribution in the entire vessel by calculating at least one of average echo height voltage values, echo height accumulated voltage values, and echo height peak voltage values in the duration range, and determining as a noise group a distribution with higher average echo height voltage values, a distribution with higher calculated echo height voltage values, or a distribution with higher peak echo height voltage values, which has been dichotomized from the statistical distribution.

According to the above noise determining method, the respective statistical distributions in the entire vessel can be created by calculating at least one of average echo height voltage values, echo height accumulated voltage values, and echo height peak voltage values in the duration range of the boundary surface echo monitoring gate set in the predetermined duration range. In the case where there is a separation between the vessel steel plate and the surface layer of the vessel steel plate formed by bonding surface layers made of different materials, a separation waveform of high echo height voltage values appears and the normal boundary surface echo waveform and the separation waveform are dichotomized in the statistical distribution.

Then, a distribution with higher average echo height voltage values, a distribution with higher calculated echo height voltage values, or a distribution with higher peak echo height voltage values can be determined as a noise group.

Since thickness is not displayed by designating the noise group, erroneous display showing thinner thicknesses than real thicknesses due to separation between the vessel steel plate the surface layer can be prevented.

Further, a repaired portion designating method according to the invention is a method, after thicknesses of a vessel steel plate are continuously measured by detecting echo height voltage values of an ultrasonic response waveform using ultrasonic probes from inside of the vessel provided with a jacket steel material on the outer circumferential part, of designating portions to be repaired from the outer side of the jacket steel material, and the method is characterized by plotting measured thicknesses of the vessel steel plate on two-dimensional coordinates for developing an inner surface side of the vessel steel plate, then, performing symmetrical coordinate transformation with respect to the two-dimensional coordinates, assuming that an inner diameter of a vessel barrel part is r, a thickness of the vessel barrel part is S1, a spaced distance between an outer surface of the vessel barrel part and an inner surface of the jacket steel material is g, a thickness of the jacket steel material is S2, creating two-dimensional coordinates for developing an outer surface of the jacket steel material by performing $(r+S1+g+S2)/r$ times magnifying coordinate transformation with respect to the two-dimensional coordinates, and designating portions to be repaired from the outer side of the jacket steel material based on the thickness of the vessel steel plate plotted on the two-dimensional coordinates.

In the repaired portion designating method, first, the thicknesses of the vessel steel plate are continuously measured using ultrasonic probes from inside of the vessel, the measured thicknesses of the vessel steel plate are plotted on two-dimensional coordinates for developing the inner surface side of the vessel barrel part.

Then, the two-dimensional coordinates on which the thicknesses of the vessel steel plate seen from the vessel inside are plotted can be coordinate transformed into two-dimensional coordinates for developing the outer surface of the jacket steel material on which the thicknesses of the vessel steel plate are plotted by performing symmetrical coordinate transformation with respect to the two-dimensional coordinates on which the thicknesses of the vessel steel plate seen from the vessel inside are plotted, assuming that an inner diameter of a vessel barrel part is r, a thickness of the vessel barrel part is S1, a spaced distance between an outer surface of the vessel barrel part and an inner surface of the jacket steel material is g, a thickness of the jacket steel material is S2, and performing $(r+S1+g+S2)/r$ times magnifying coordinate transformation with respect to the two-dimensional coordinates.

Then, based on the thicknesses of the vessel steel plate plotted on the coordinate transformed two-dimensional coordinates, the portions to be repaired can be accurately designated from the outer side of the jacket steel material, and the repairing can be conducted more efficiently compared to the conventional empirical repairing method.

BRIEF DESCRIPTION OF THE DRAWINGS

FIGS. 6(*a*) to 6(*c*) are a plan view, a side view, and a front view showing a structure of a supporting point member detachable from a supporting point set at the central axis of the vessel mirror part.

FIG. 22 show an example of a measurement result.

FIG. 28 show ultrasonic response waveforms by the ultrasonic probes at the boundary surface between the surface layer and the vessel steel plate, FIG. 28(a) shows an example of the ultrasonic response waveform in the case where there is a separation between the vessel steel plate and the surface layer, FIG. 28(b) shows an example of the ultrasonic response waveform in the case where there is no separation between the vessel steel plate and the surface layer, and FIG. 28(c) shows an example of the ultrasonic response waveform in the case where there is a flaw such as an inclusion or lamination in the vessel steel plate.

BEST MODE FOR CARRYING OUT THE INVENTION

As an example of a thickness measuring device for vessel steel plate according to the invention, one embodiment of the thickness measuring device for vessel steel plate will be specifically described in the case where it is applied to a reactor (reaction vessel) including a vessel mirror part (vessel bottom) formed by a spherical curved surface and a circular projection form and having a vessel barrel part substantially in a cylindrical form that continues in a direction substantially perpendicular to the vessel mirror part and an obstruction such as a baffle provided to the vessel barrel.

Figure 1:
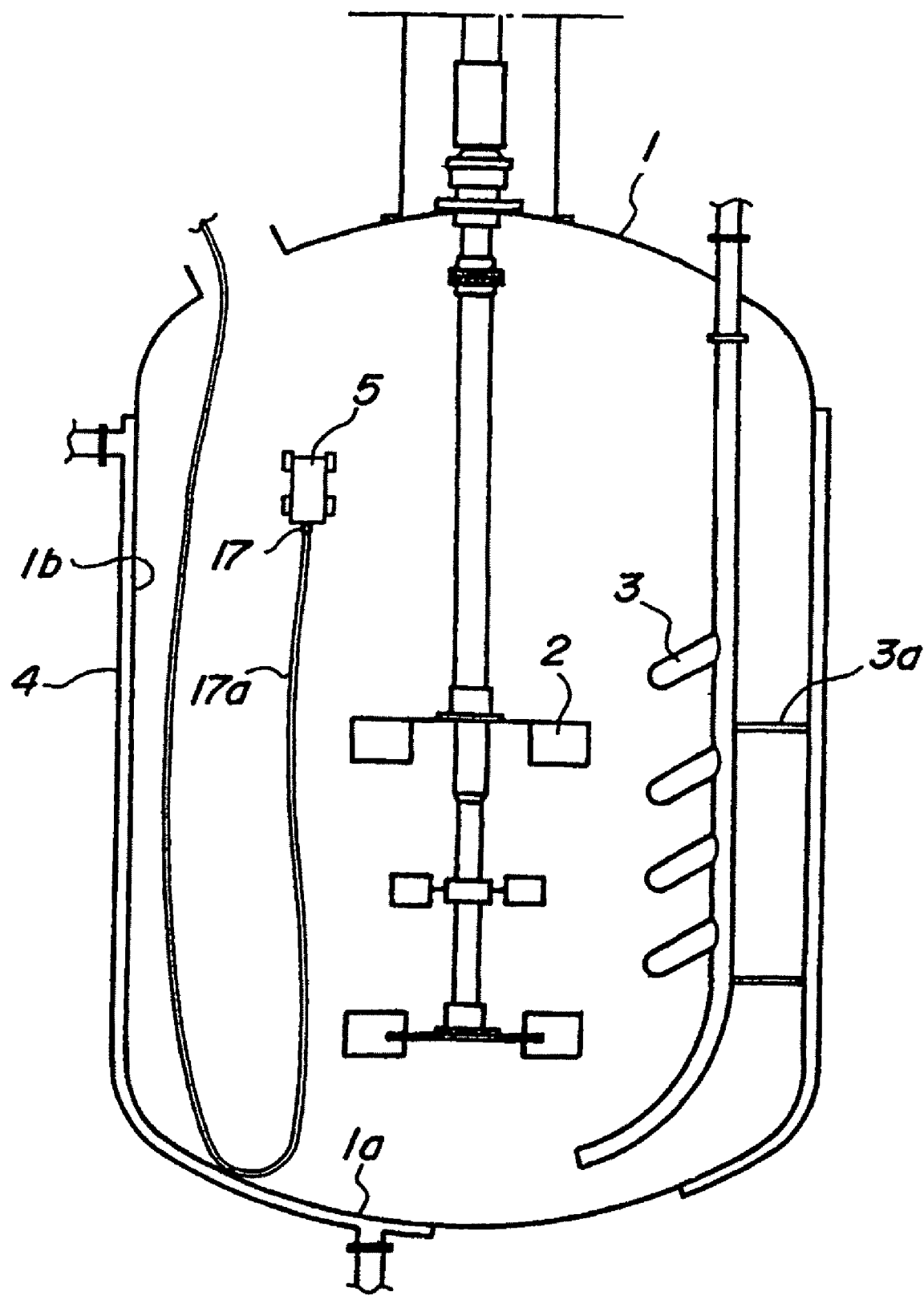
FIG. 1 is a sectional explanatory view showing a status in which a thickness of a vessel barrel part of a reactor is measured by a thickness measuring device for vessel steel plate according to the invention.
Figure 2:
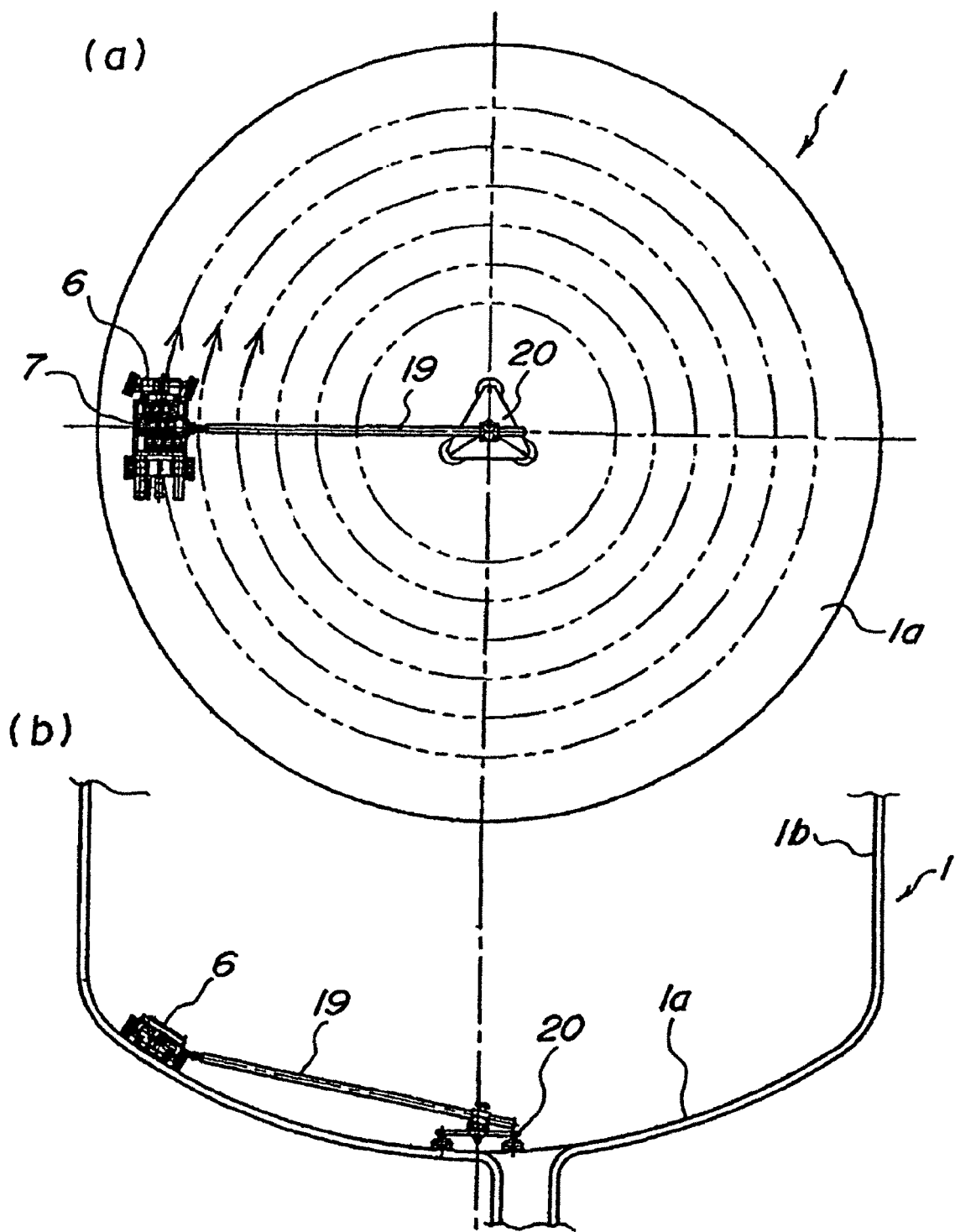
FIGS. 2(*a*) and 2(*b*) are a plan view and a sectional side view showing a state in which a thickness of a vessel mirror part of the reactor is measured by the thickness measuring device for vessel steel plate according to the invention.

In FIGS. 1 and 2, 1 denotes a reactor (reaction vessel) and the reactor includes a vessel mirror part 1a formed by a curved surface having a predetermined curvature and having a circular projection form, and a vessel barrel part 1b substantially in a cylindrical form that continues in a height direction to the vessel mirror part 1a.

An example of the case where the vessel mirror part 1a is formed by a spherical curved surface of the embodiment will be described, however, the invention can be applied similarly to a vessel mirror part formed by a conical curved surface. Further, an agitator 2 rotationally driven by a motor (not shown) is provided at the central axis part of the reactor 1 of the embodiment, and a baffle 3 as an as a filing pipe also serving for accelerating agitation is supported by the vessel barrel part 1b.

In the embodiment, the agitator 2 and baffle 3 are obstructions in thickness measurement. However, although not shown, agitating blades, a gas suction pipe, a thermometer, etc. may be provided within the reactor 1 as other obstructions.

A jacket steel material 4 for circulating hot water or water is provided by welding or the like around the circumference from the vessel mirror part 1a to the vessel barrel part 1b of the reactor 1 for the purpose of heat retaining or temperature adjustment of reaction temperature.

A traveling carriage 5 shown in FIG. 1 is a traveling carriage having plural ultrasonic probes 7 mounted thereon and traveling in a vertical direction (height direction) or horizontal direction (circumference direction) on the steel plate of the vessel barrel part 1b. Similarly, a traveling carriage 6 shown in FIG. 2 is a traveling carriage having plural ultrasonic probes 7 mounted thereon and traveling in a circumference direction on the steel plate of the vessel mirror part 1a with a predetermined radius of curvature.

The ultrasonic probe 7 is supported by a small carriage 7a also serving as a probe unit, and the small carriage 7a is supported by a support frame of an ultrasonic probe unit 13 via a gimbal mechanism. In the ultrasonic probe unit 13 of the embodiment, twelve ultrasonic probes 7 are arranged in a staggered manner (alternately) and integrally mounted.

Figure 3:
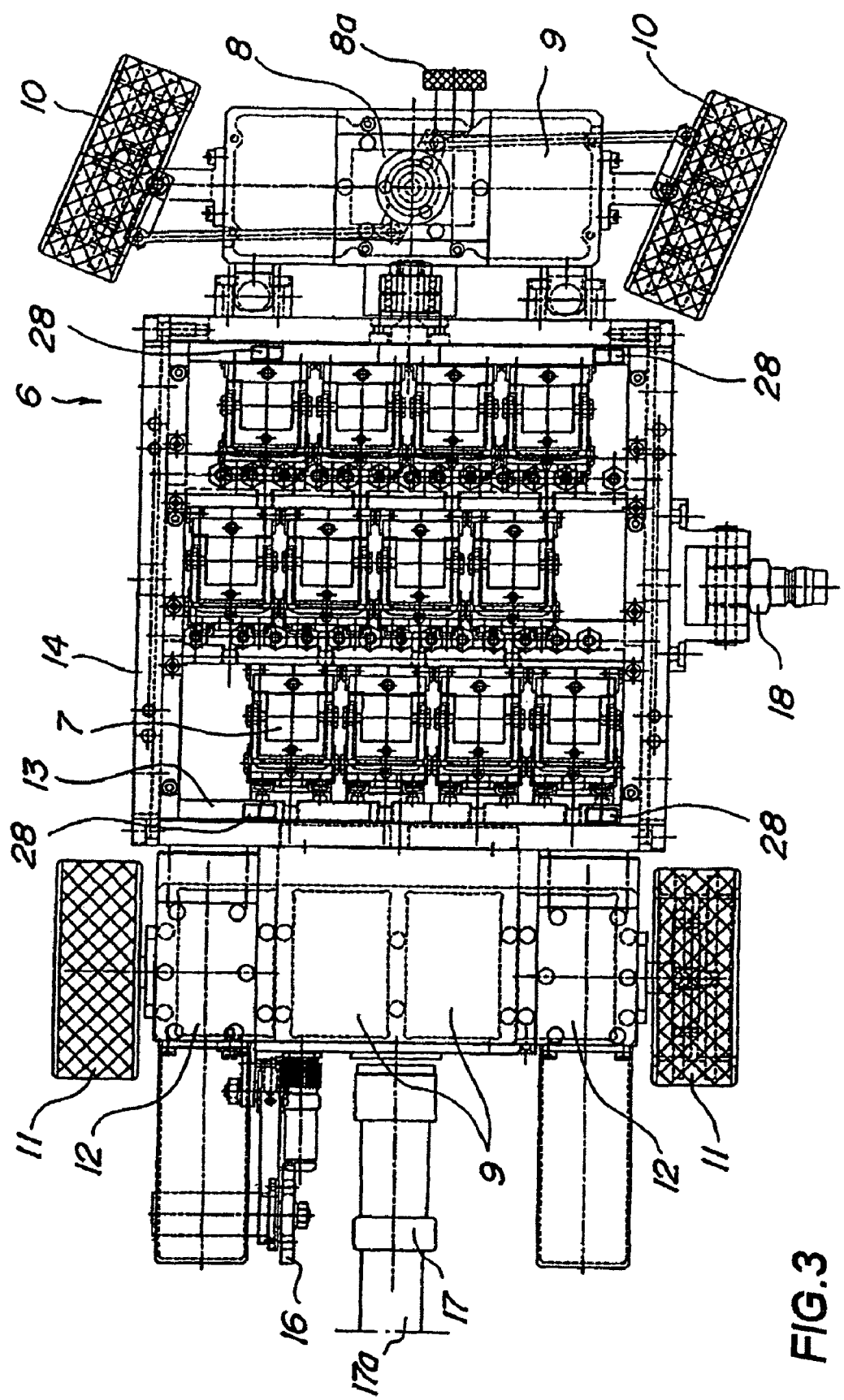
FIG. 3 is a plan view showing a structure of a first traveling carriage capable of traveling on a steel plate of the vessel mirror part formed by a spherical curved surface.
Figure 4:
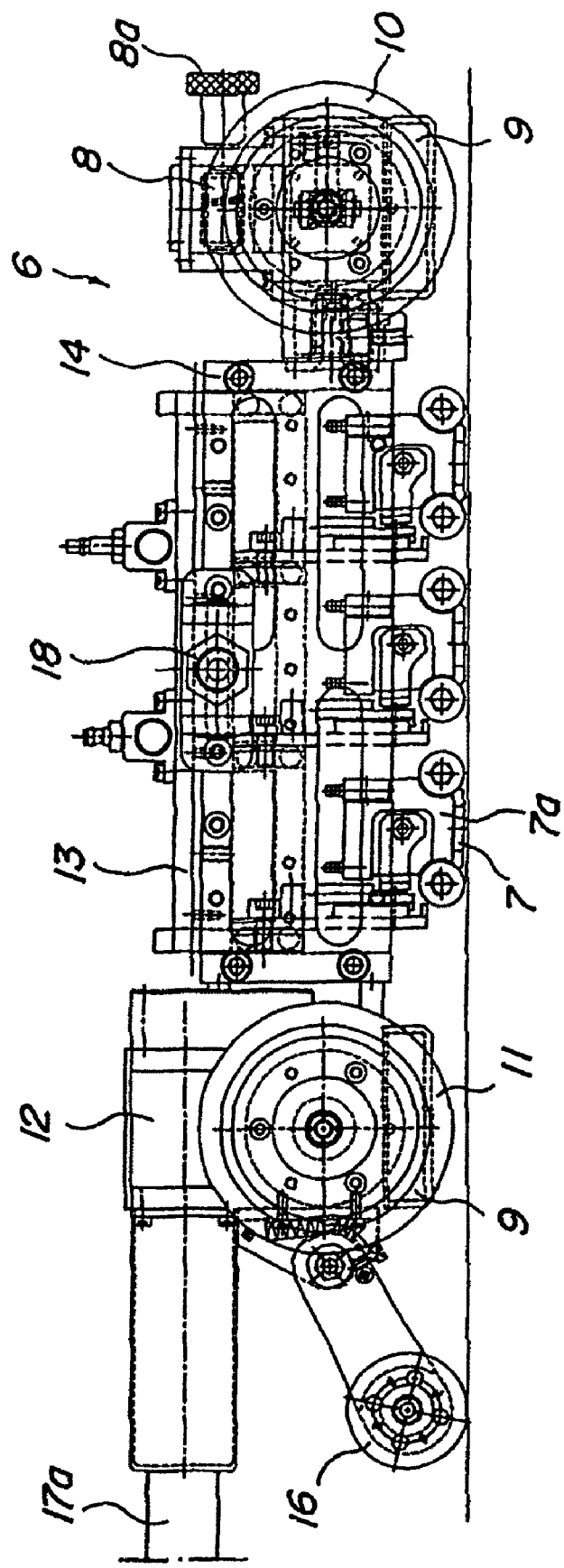
FIG. 4 is a side view showing the structure of the first traveling carriage capable of traveling on the steel plate of the vessel mirror part formed by a spherical curved surface.
Figure 5:
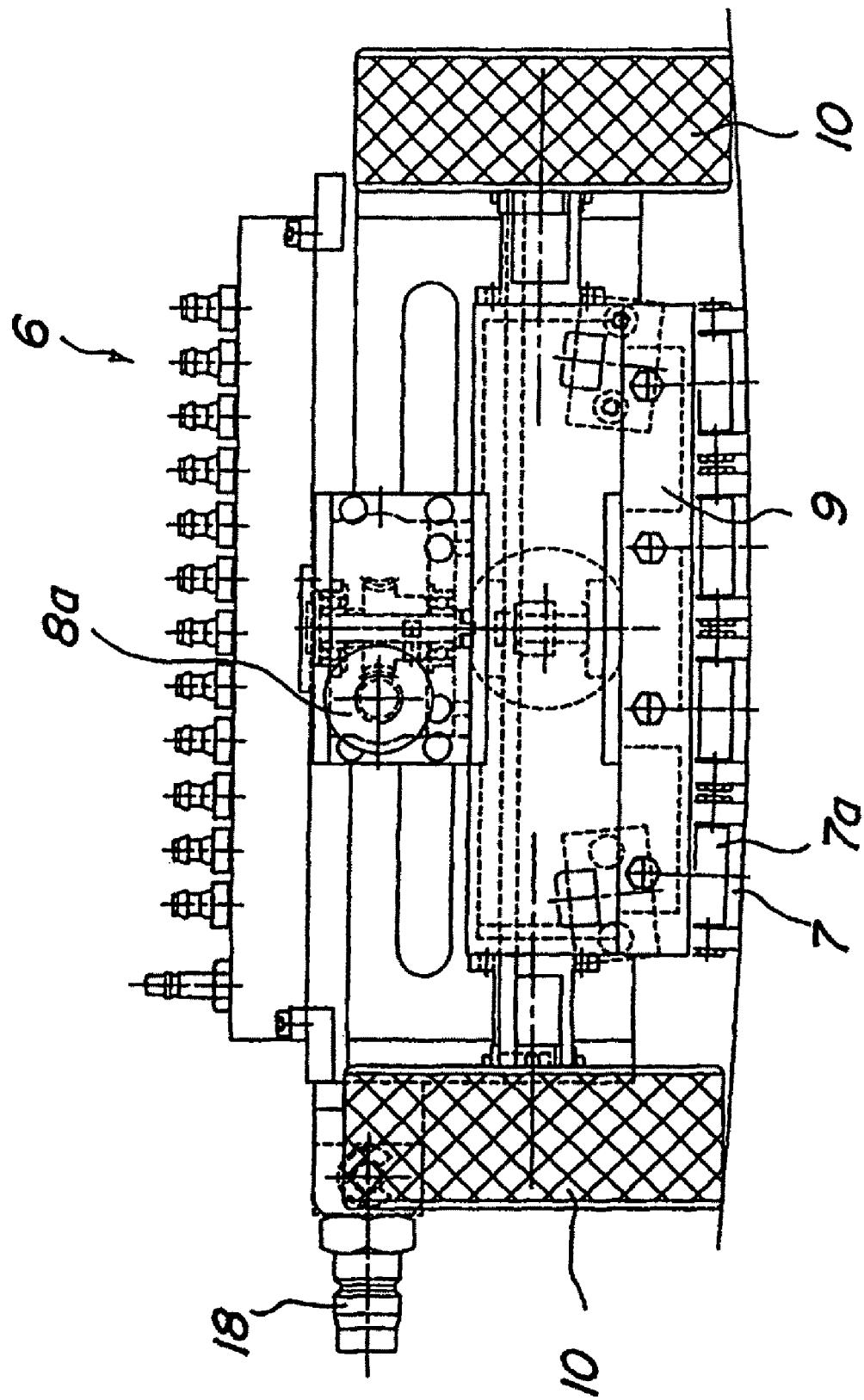
FIG. 5 is a front view showing the structure of the first traveling carriage capable of traveling on the steel plate of the vessel mirror part formed by a spherical curved surface.

As shown in FIGS. 3 to 5, the traveling carriage 6 traveling on the steel plate of the vessel mirror part 1a is provided with a steering mechanism 8 that can change the radius of curvature of the traveling track at front wheels 10 thereof, and the steering angle of the front wheels 10 can be adjusted by sliding a steering angle adjustment knob 8a connected to a link mechanism of the steering mechanism 8 upward and downward in FIG. 3.

On the other hand, left and right rear wheels 11 are provided with traveling motors 12 as a traveling driving mechanism that can independently and rotationally drive the left and right rear wheels 11, respectively.

9 denotes a magnet as a magnetic material that exerts an attraction force by a magnetic force on the vessel steel plate. However, as the magnetic material, a permanent magnet or electromagnet can be adopted. Further, four wheels of the front and rear wheels 10 and 11 may be formed by magnets, respectively.

13 denotes the ultrasonic probe unit on which plural ultrasonic probes 7 are integrally mounted, and the ultrasonic probe unit 13 is detachably formed from a main body frame 14 of the traveling carriage 6. However, the ultrasonic probe unit 13 is also detachably formed from a carriage member 15 of the traveling carriage 6, which will be described later as shown in FIGS. 7 to 12, and thereby, the common ultrasonic probe unit 13 can be selectively attached to or detached from the traveling carriage 6 traveling on the vessel mirror part 1a and the traveling carriage 5 traveling on the vessel barrel part 1b.

As attaching and detaching means for attaching the ultrasonic probe unit 13 to and detaching it from the traveling carriages 5 and 6, bolting or screwing may be adopted, however, in the embodiment, buckles 28 are used for detachable arrangement through a single touch operation. Various kinds of attaching and detaching means other than that can be applied.

16 denotes an encoder as a distance measurement mechanism, and 17 denotes a control cable connector to which a power supply cable or signal cable 17a is connected. The control cable connector 17 of the traveling carriage 6 connects a power supply cable of the traveling motor 12 and a signal cable for transmitting control signals, and further, a signal cable for transmitting control signals of the ultrasonic probes 7 and thickness measurement data by the ultrasonic probes 7, a signal cable for transmitting traveling distance data measured by the encoder 16, etc.

A rotation guide joint 18 is provided on the side part of the main body frame 14 of the traveling carriage 6, and one end of a turning radius regulating member 19 shown in FIG. 6 is connected to the rotation guide joint 18.

Figure 20:
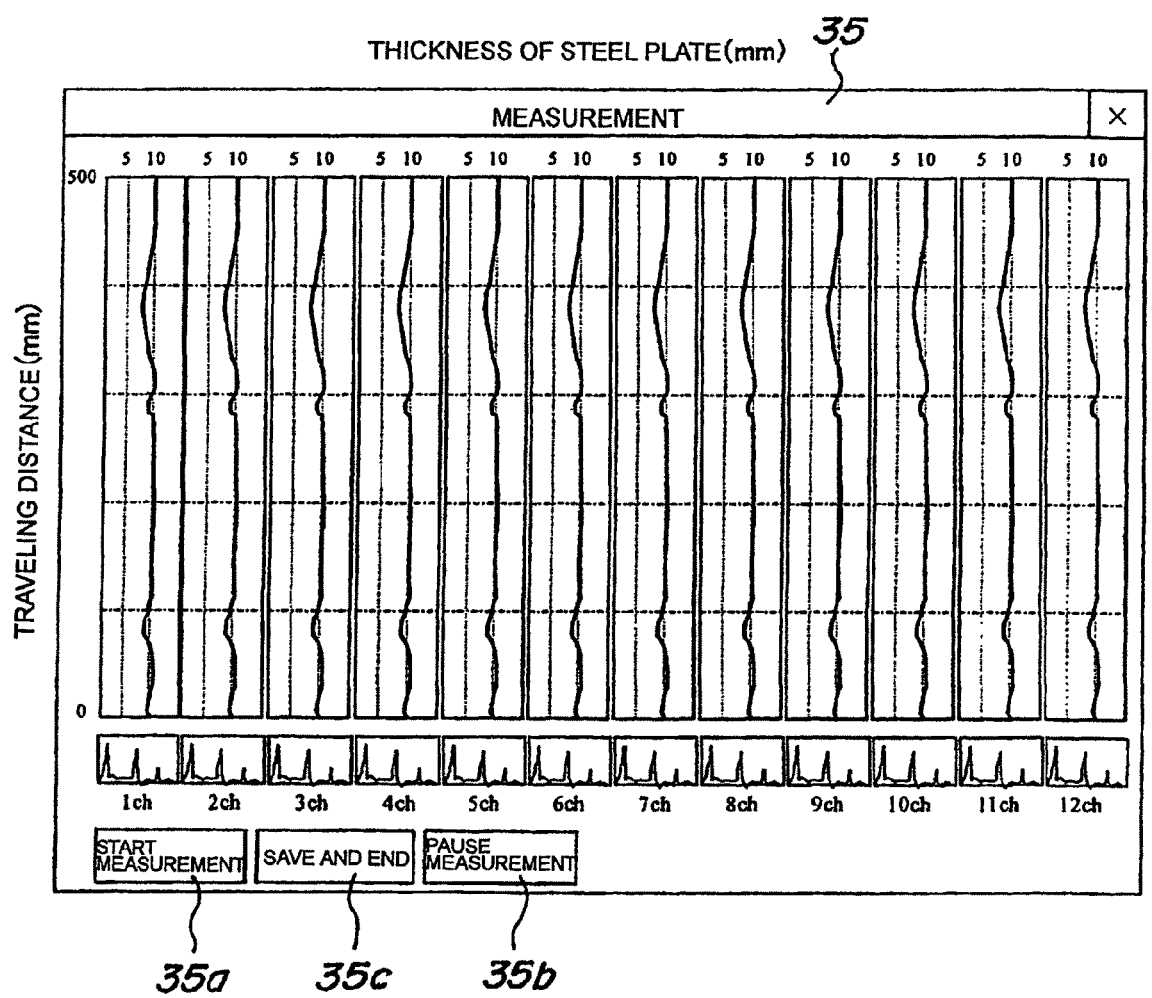
FIG. 20 shows an example of a measurement screen of sampling software during measurement.

In FIGS. 6, 20 denotes a supporting point member detachable from a supporting point set at the central axis of the vessel mirror part 1a, and formed easily detachably from the vessel mirror part 1a by the attraction force by the magnetic material such as a permanent magnet and electromagnet, or attraction force by a sucker or the like.

The other end of the turning radius regulating member 19 is supported by a holder member 21 rotatively provided to the supporting point member 20, and the spaced distance between the supporting point set at the central axis of the vessel mirror part 1a and the traveling carriage 6 can be regulated by adjusting the fixed length of the turning radius regulating member 19 by a length adjustment knob 21a.

According to the above configuration, when the steel plate thickness of the vessel mirror part 1a formed by a spherical or conical curved surface having a circular projection form is measured, the supporting point member 20 is mounted to the supporting point set at the central axis of the vessel mirror part 1a, and the traveling carriage 6 is traveled on the circumference with a predetermined radius of curvature while the traveling radius of the traveling carriage 6 on which ultrasonic probes are mounted is regulated by the turning radius regulating member 19, and thereby, the steel plate thickness of the vessel mirror part 1a around a lap of the radius of curvature can be measured. The steel plate thickness can be measured substantially over the entire surface of the vessel mirror part 1a by continuously increasing or decreasing the spaced distance between the traveling carriage 6 and the supporting point set at the central axis of the vessel mirror part 1a by the turning radius regulating member 19.

In FIGS. 7 to 12, the traveling carriage 5 traveling on the steel plate of the vessel barrel part 1b is provided with the magnet 9 as a magnetic material that acts an attraction force by a magnetic force on the vessel steel plate as well as the above described traveling carriage 6. However, as the magnetic material, a permanent magnet or electromagnet can be adopted. Further, four wheels of the front and rear wheels 10 and 11 may be formed by magnets, respectively.

The four front and rear wheels 10 and 11 are provided with traveling motors 12 as a traveling driving mechanism that can independently and rotationally drive the four wheels 10 and 11, respectively. The traveling driving mechanism that can make the left and right wheels to move forward/backward independently is formed by controlling the four traveling motors 12 to normally/reversely rotate.

Figure 10:
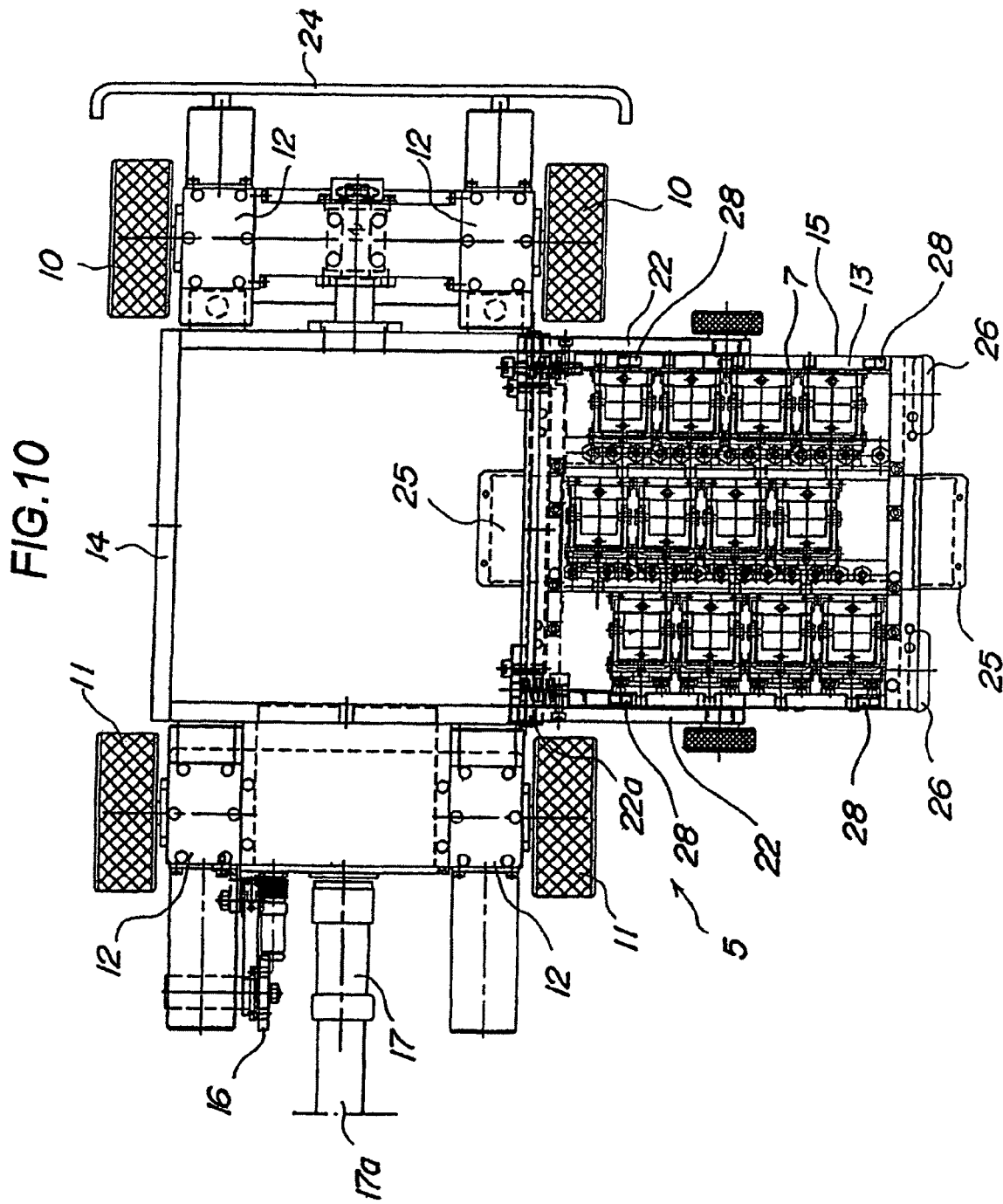
FIG. 10 is a plan view showing a structure in which a carriage member on which plural ultrasonic probes are mounted is moved in a direction crossed to the traveling direction of the traveling carriage and projected in the second traveling carriage capable of traveling on the steel plate of the vessel mirror part substantially in a cylindrical form that continues in a direction substantially perpendicular to the vessel mirror part.
Figure 11:
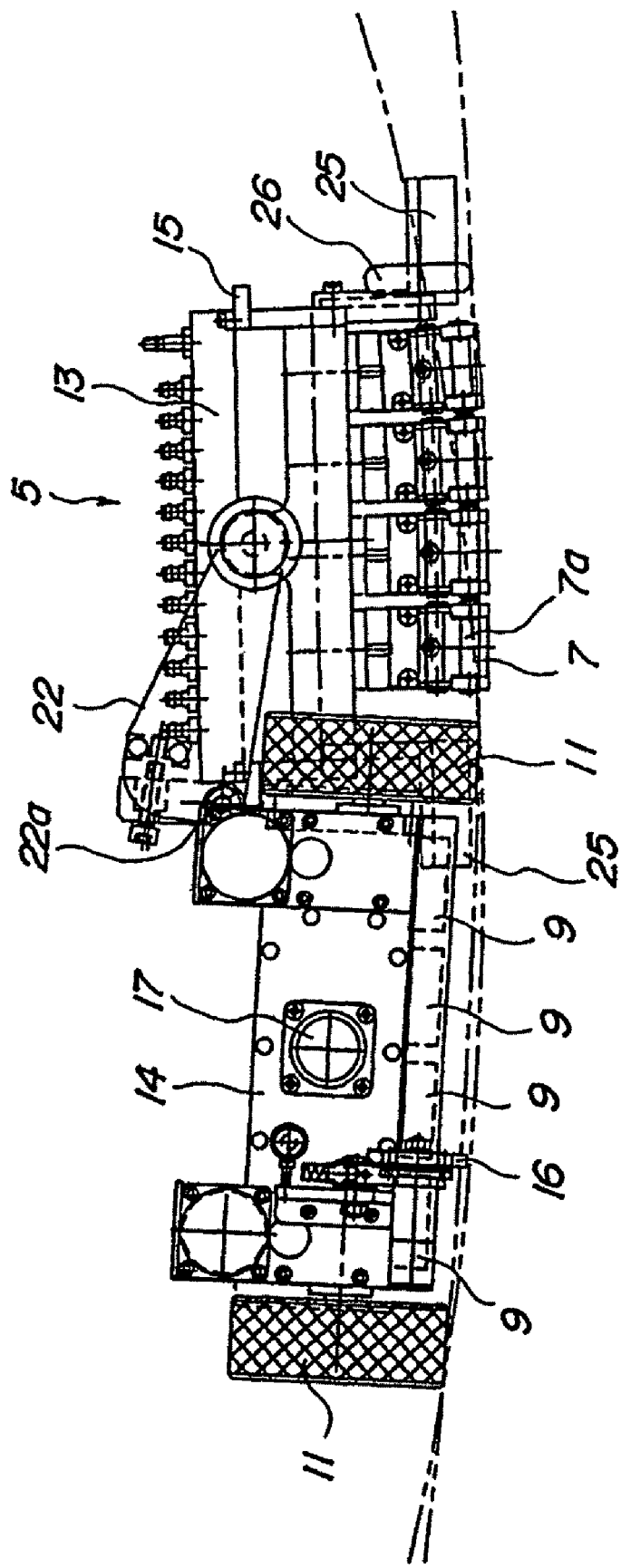
FIG. 11 is a rear view showing the structure in which the carriage member on which plural ultrasonic probes are mounted is moved in the direction crossed to the traveling direction of the traveling carriage and projected in the second traveling carriage capable of traveling on the steel plate of the vessel mirror part substantially in a cylindrical form that continues in a direction substantially perpendicular to the vessel mirror part.

As shown in FIGS. 10 and 11, a rotative arm 22 as moving means and rotating means is rotatively provided around a rotative shaft 22a to the main body frame 14 of the traveling carriage 5, and the carriage member 15 is provided swingably relative to the rotative arm 22 at the end of the rotative arm 22.

The ultrasonic probe unit 13 on which plural ultrasonic probes are mounted is detachably formed from a carriage member 15, and the attaching and detaching means is detachably arranged using buckles 28 through a single touch operation as well as the attaching and detaching means for the above described ultrasonic probe unit 13 and the main body frame 14. Other various kinds of attaching and detaching means can be applied as well as described above.

Further, the rotative arm 22 is rotated and the carriage member 15 on which the ultrasonic probe unit 13 is mounted is moved in a direction crossed to the traveling direction of the traveling carriage 5 (perpendicular direction in the embodiment), and thereby, the carriage member 15 can be projected toward the width direction of the traveling carriage 5.

Further, a collision sensor 24 having a bumper form as obstruction detecting means for detecting obstructions in the traveling direction of the traveling carriage 5 is provided at the front end of the main body frame 14. A control part 31 shown in FIG. 16 drive controls the traveling motors 12 of the traveling carriage 5 to prevent the runaway and fall of the traveling carriage 5 based on the obstruction detection information by the collision sensor 24, and informs the existence of obstruction by sounding an alarm or the like from a speaker 27e of a controller 27 or emitting light from an LED (light emitting diode) 27a shown in FIG. 15 as an example of informing means or the like.

Further, when the traveling carriage 5 collides with an obstruction, the overload current of the traveling motor 12 can be detected for drive control of the traveling motor 12. Furthermore, as other configuration of the obstruction detection means for detecting obstructions in the traveling direction of the traveling carriage 5, an ultrasonic sensor, infrared sensor, or the like may be adopted.

The control cable connector 17 of the traveling carriage 5 connects a power supply cable of the traveling motor 12 and a signal cable for transmitting control signals, a signal cable for transmitting obstruction detection information detected by the collision sensor 24, and further, a signal cable for transmitting control signals of the ultrasonic probes 7 and thickness measurement data by the ultrasonic probes 7, a signal cable for transmitting traveling distance data measured by the encoder 16, etc.

Auxiliary magnets 25 as magnetic materials that act an attraction force by a magnetic force on the vessel steel plate are mounted on the support frame of the carriage member 15. However, as the magnetic material, a permanent magnet or electromagnet can be adopted. Further, auxiliary wheels 26 are provided to the support frame of the carriage member 15. The auxiliary wheels 26 may be formed by magnets.

Figure 8:
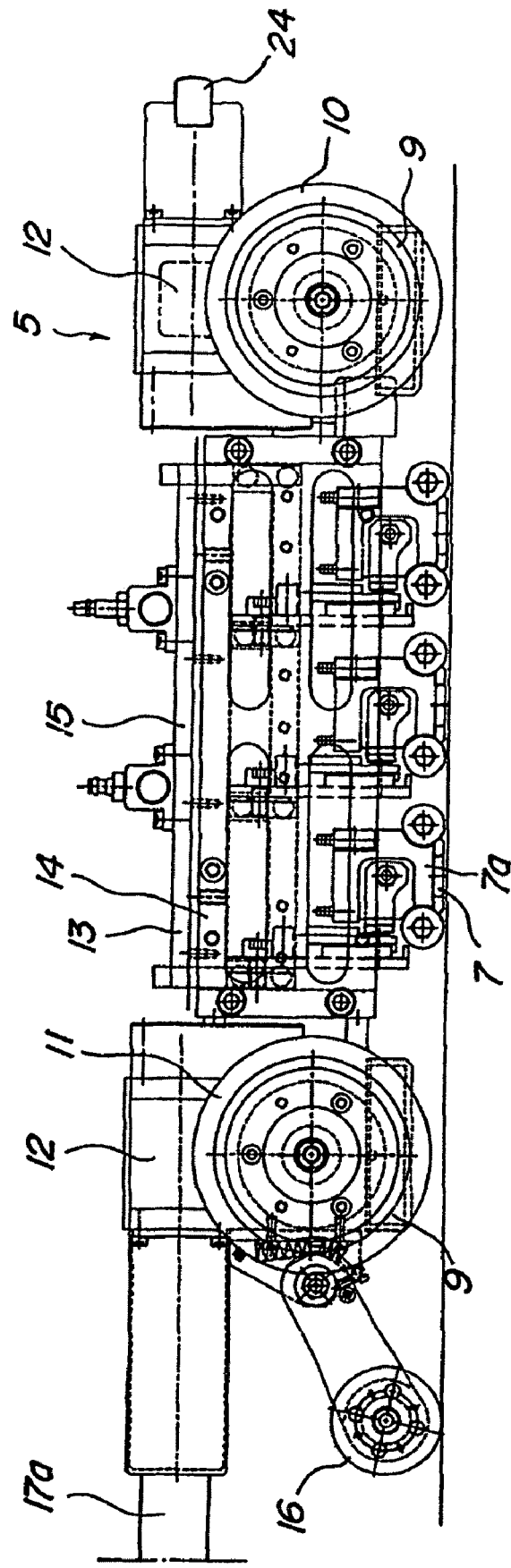
FIG. 8 is a side view showing the structure of the second traveling carriage capable of traveling on the steel plate of the vessel mirror part substantially in a cylindrical form that continues in a direction substantially perpendicular to the vessel mirror part.
Figure 9:
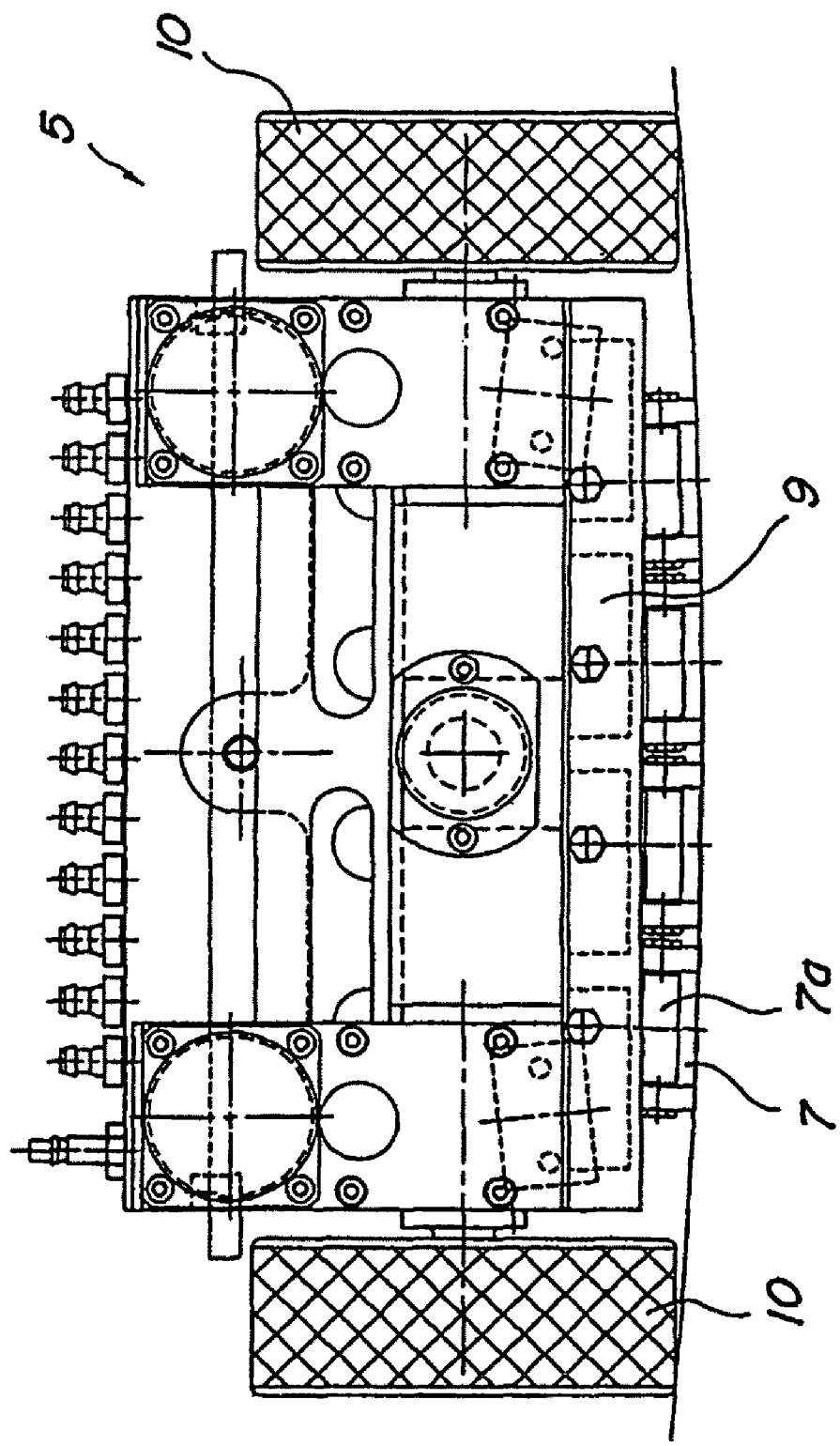
FIG. 9 is a front view showing the structure of the second traveling carriage capable of traveling on the steel plate of the vessel mirror part substantially in a cylindrical form that continues in a direction substantially perpendicular to the vessel mirror part.
Figure 12:
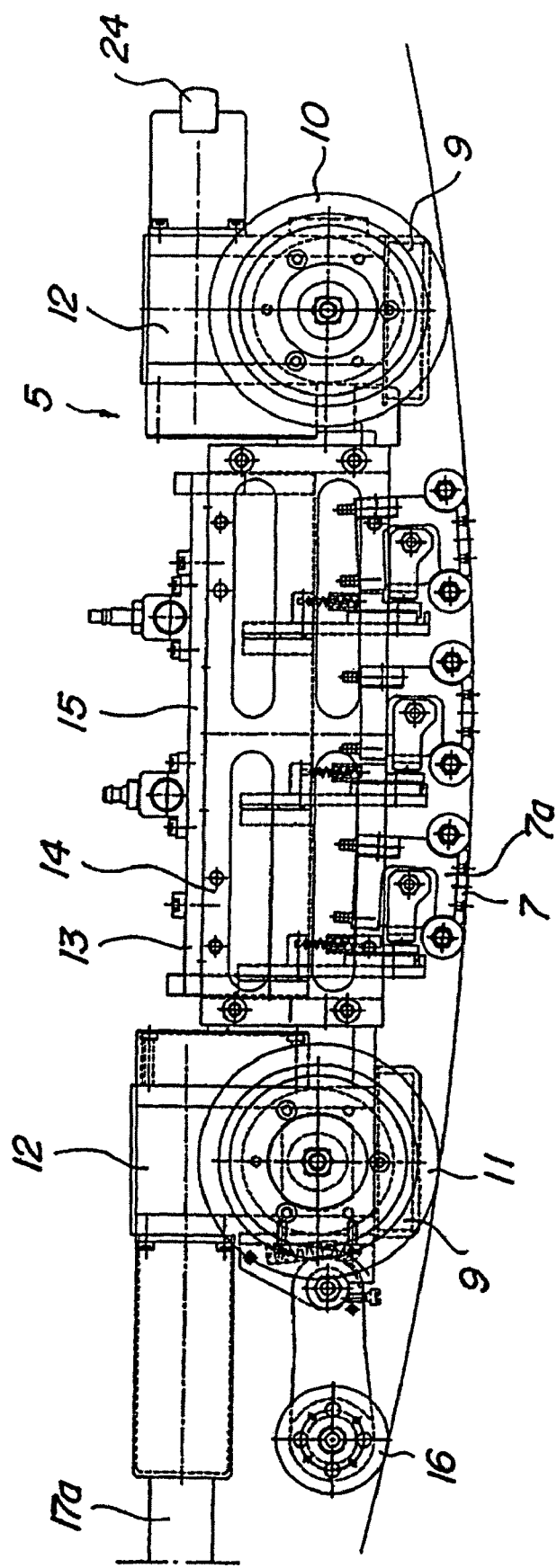
FIG. 12 is a side view showing a state in which the second traveling carriage travels on the steel plate of the vessel barrel part in a circumference direction.

FIGS. 8, 9, and 11 show a state in which the traveling carriage 5 travels in the vertical direction (height direction) on the steel plate of the vessel barrel part 1b, and FIG. 12 shows a state in which the traveling carriage 5 travels in the horizontal direction (circumference direction) on the steel plate of the vessel barrel part 1b.

Figure 13:
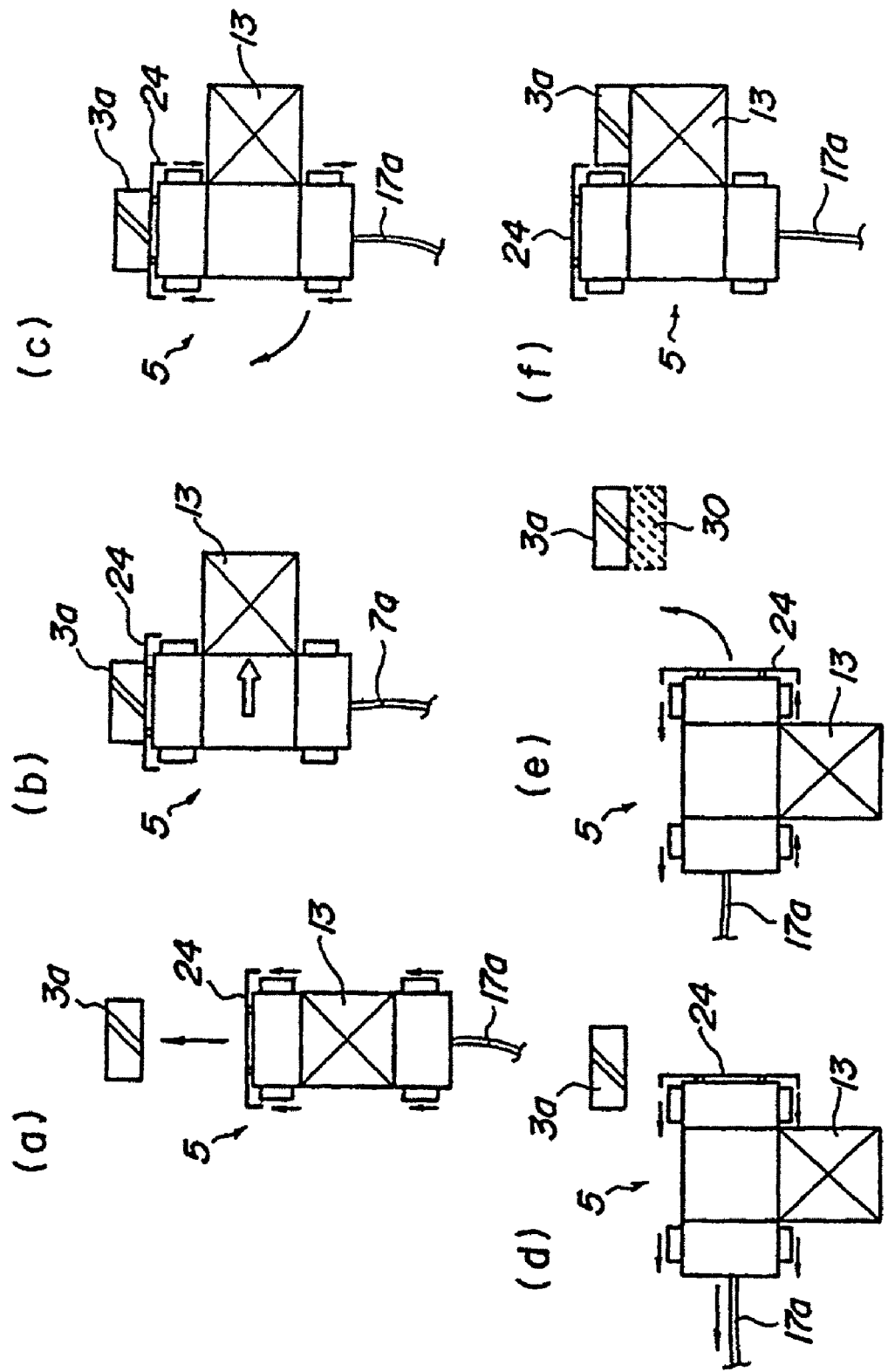
FIG. 13 are schematic plan views showing a state in which the second traveling carriage measures the thickness of the vessel barrel part by projecting the plural ultrasonic probes toward the width direction while avoiding obstructions.
Figure 14:
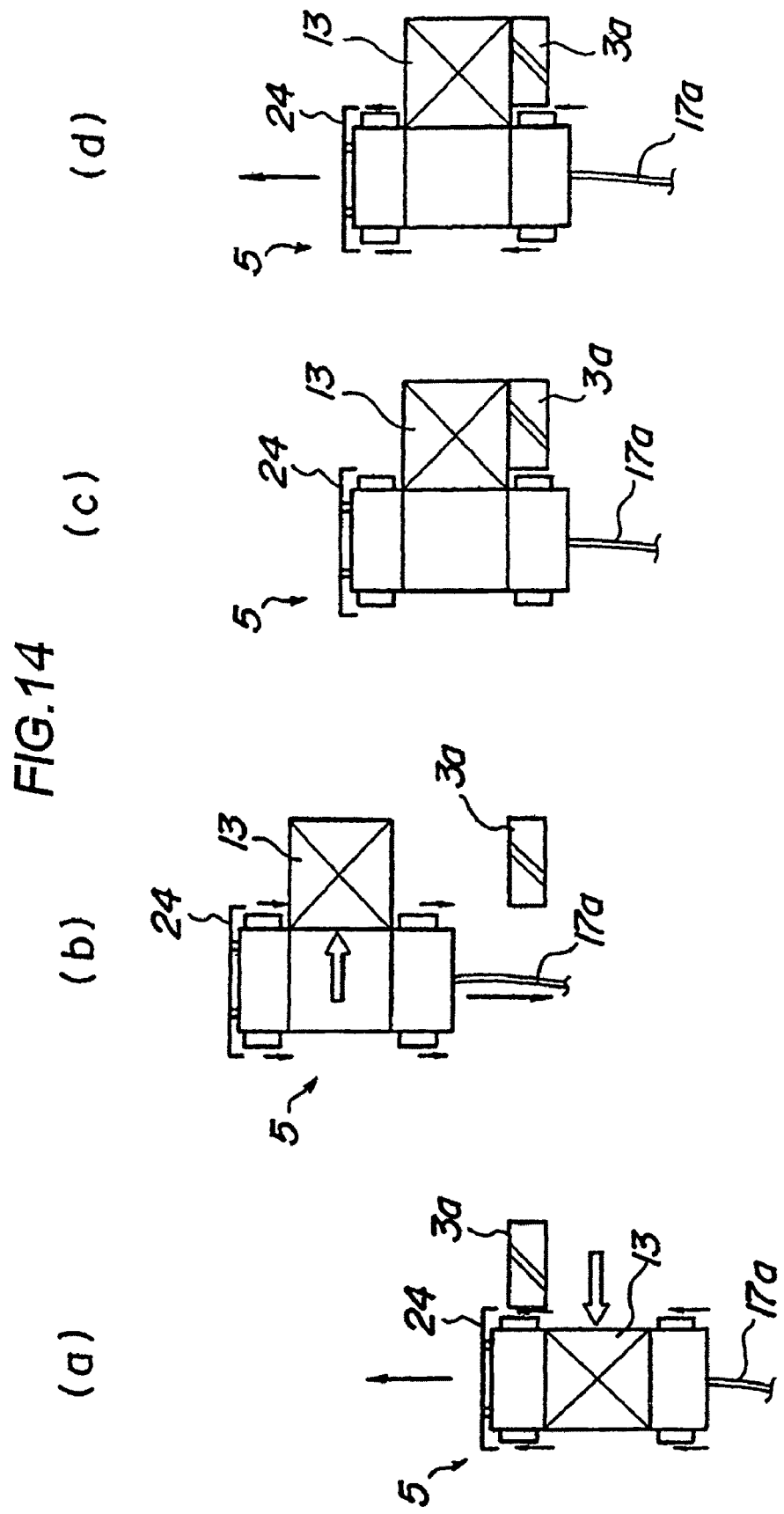
FIG. 14 are schematic plan views showing a state in which the second traveling carriage measures the thickness of the vessel barrel part by projecting the plural ultrasonic probes toward the width direction while avoiding obstructions.

FIGS. 13 and 14 show a state in which the traveling carriage 5 traveling on the steel plate of the vessel barrel part 1b projects the ultrasonic probe unit 13 toward the width direction of the traveling carriage 5 while avoiding a support member 3a for supporting the baffle 3 as an obstruction provided to the vessel barrel part 1b, and measures the thickness of a line of the support member 3a as an obstruction.

The collision sensor 24 having a bumper form is provided at the front surface of the traveling carriage 5. As shown in FIG. 13(a), the traveling carriage 5 has traveled while measuring the thickness of a line of the support member 3a of the supporting the baffle 3, which becomes an obstruction in a state in which the ultrasonic probe unit 13 is mounted in the home position, and the collision sensor 24 at the front surface collides with the support member 3a and detects the obstruction. Here, an unmeasured part 30 shown in FIG. 13(e) left between the traveling carriage 5 and the support member 3a as the obstruction is recorded in a personal computer (hereinafter, referred to as "PC") 34.

Thus recorded unmeasured part 30 in the PC 34 can be remeasured by rotating the rotative arm 22 around the rotative shaft 22a in a clockwise direction in FIG. 11, projecting the carriage member 15 on which the ultrasonic probe unit 13 is mounted toward the width direction of the traveling carriage 5, and shifting the carriage way.

Figure 15:
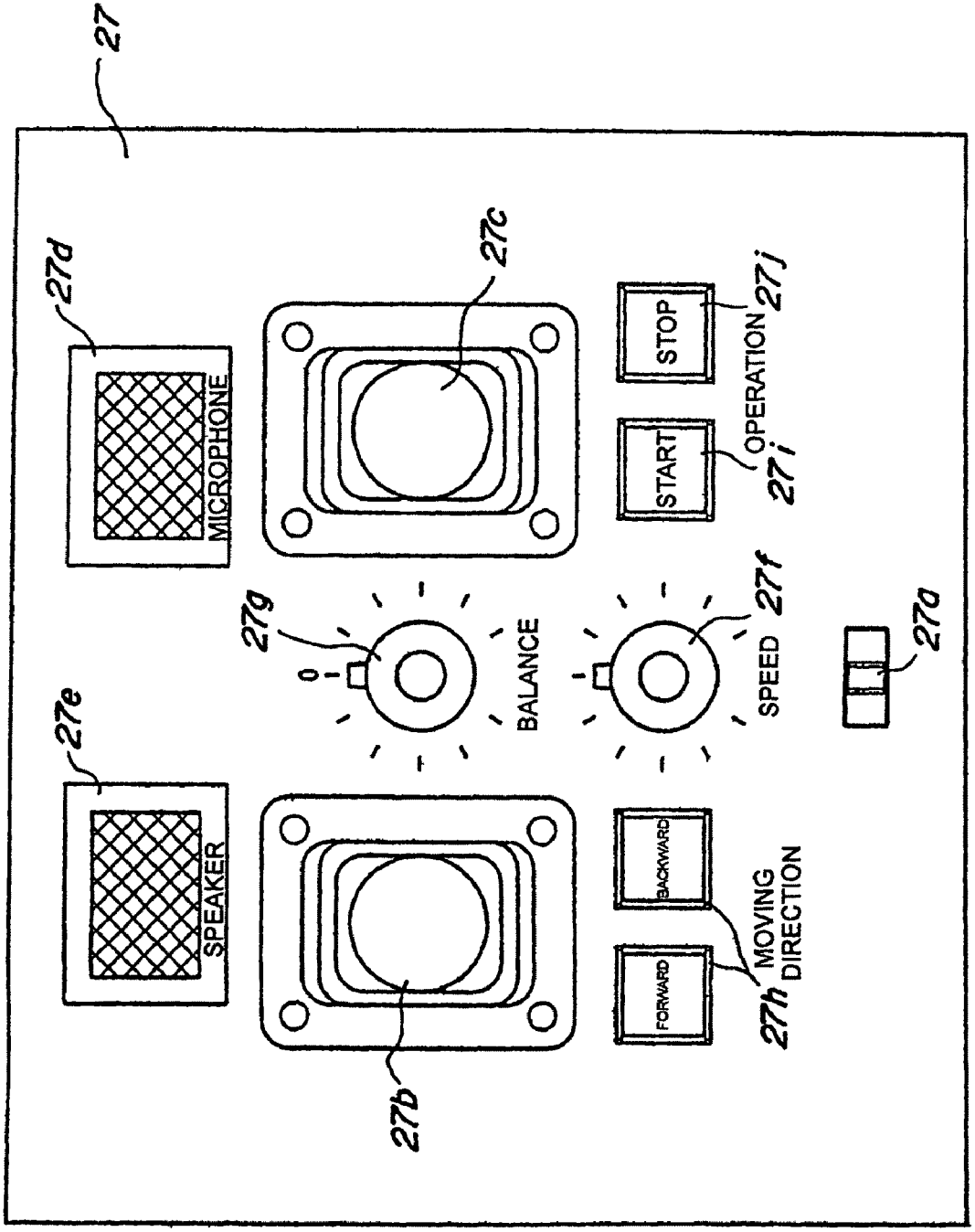
FIG. 15 shows a configuration of a controller of the traveling carriage.

Further, the measurement direction by the traveling carriage 5 can be changed to 90° according to the positional relationship of the unmeasured part 30. In this case, left and right wheel operation sticks 27b and 27c of the controller 27 shown in FIG. 15 are operated for independently moving the traveling carriage 5 forward/backward. First, by tilting the left wheel operation stick 27b toward the forward direction (upward direction in FIG. 15) and tilting the right wheel operation stick 27c toward the backward direction (downward direction in FIG. 15), both front and rear wheels on the left of the traveling carriage 5 are rotationally driven in the forward direction and both front and rear wheels on the right of the traveling carriage 5 are rotationally driven in the backward direction (FIG. 13(c)) and rotated to 90° to the right with an extremely small turning radius (FIG. 13 (d)).

Furthermore, by tilting the left and right wheel operation sticks 27b and 27c toward the backward direction (downward direction in FIG. 15) to rotationally drive all wheels of the traveling carriage 5 in the backward direction, the traveling carriage 5 is moved backward by a predetermined distance from which the traveling carriage 5 can be turned to a position where the thickness measurement of the unmeasured part 30 can be performed by the projected ultrasonic probe unit 13 while the traveling carriage 5 avoiding the support member 3a as the obstruction and traveling (FIG. 13(e)).

Then, by tilting the left wheel operation stick 27b of the controller in FIG. 15 toward the backward direction (downward direction in FIG. 15) and tilting the right wheel operation stick 27c toward the forward direction (upward direction in FIG. 15), both front and rear wheels on the left of the traveling carriage 5 are rotationally driven in the backward direction and both front and rear wheels on the right of the traveling carriage 5 are rotationally driven in the forward direction (FIG. 13(*e*)) and rotated to 90° to the left with an extremely small turning radius (FIG. 13 (*f*)).

At this time, as shown in FIG. 13(*f*), the traveling carriage 5 changes the carriage way to a position where the thickness measurement of the unmeasured part 30 can be performed by the projected ultrasonic probe unit 13 while the traveling carriage 5 avoiding the support member 3*a* as the obstruction and traveling, and further, by tilting the left and right wheel operation sticks 27*b* and 27*c* of the controller 27 toward the forward direction (upward direction in FIG. 15) to rotationally drive all wheels of the traveling carriage 5 toward the forward direction for moving the traveling carriage 5 forward, the thickness of the unmeasured part 30 left in front of the support member 3*a* as the obstruction is measured by the projected ultrasonic probe unit 13.

Figure 7:
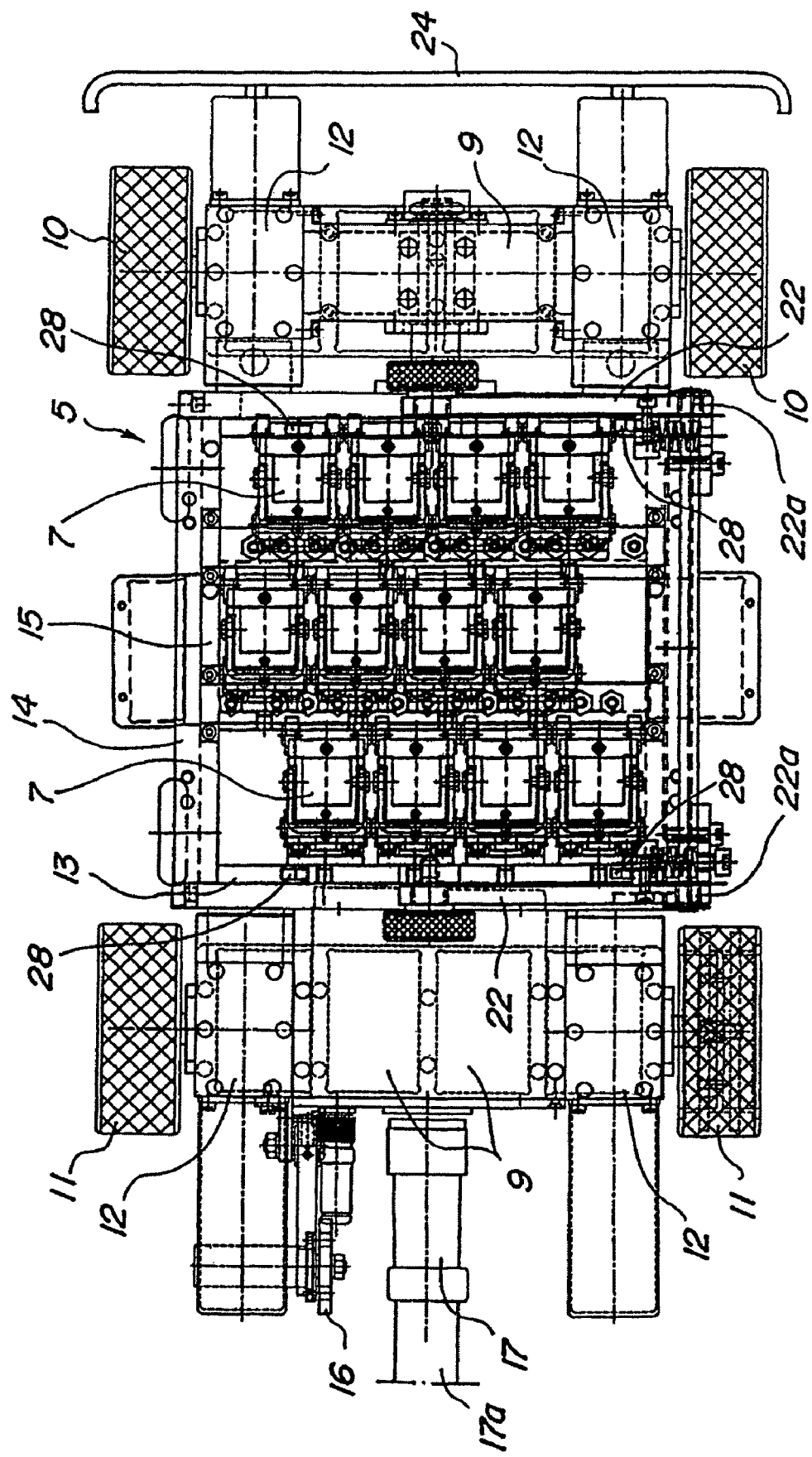
FIG. 7 is a plan view showing a structure of a second traveling carriage capable of traveling on a steel plate of a vessel barrel part substantially in a cylindrical form that continues in a direction substantially perpendicular to the vessel mirror part.

At the time when the thickness measurement of the unmeasured part 30 is measured, by rotating the rotative arm 22 around the rotative shaft 22*a* in a counter-clockwise direction in FIG. 11, the carriage member 15 on which the ultrasonic probe unit 13 projected toward the width direction of the traveling carriage 5 is accommodated in the home position as shown in FIG. 7 (FIG. 14(*a*)).

Then, by tilting the left and right wheel operation sticks 27*b* and 27*c* of the controller 27 shown in FIG. 15 toward the forward direction (upward direction in FIG. 15) to rotationally drive all wheels of the traveling carriage 5 toward the forward direction for moving the traveling carriage 5 forward, at the time when the carriage passes the support member 3*a* as the obstruction, by rotating the rotative arm 22 around the rotative shaft 22*a* in a clockwise direction in FIG. 11 again, the carriage member 15 on which the ultrasonic probe unit 13 is projected toward the width direction of the traveling carriage 5 (FIG. 14(*b*)).

Then, by tilting the left and right wheel operation sticks 27*b* and 27*c* of the controller 27 shown in FIG. 15 toward the backward direction (downward direction in FIG. 15) to rotationally drive all wheels of the traveling carriage 5 toward the backward direction for moving the traveling carriage 5 backward until the ultrasonic probe unit 13 comes near the support member 3*a* as the obstruction (FIG. 14(*c*)), and then, by tilting the left and right wheel operation sticks 27*b* and 27*c* of the controller 27 toward the forward direction (upward direction in FIG. 15) to rotationally drive all wheels of the traveling carriage 5 toward the forward direction for moving the traveling carriage 5 forward again, the unmeasured part at the other side of the support member 3*a* as the obstruction is measured (FIG. 14(*d*)).

Figure 16:
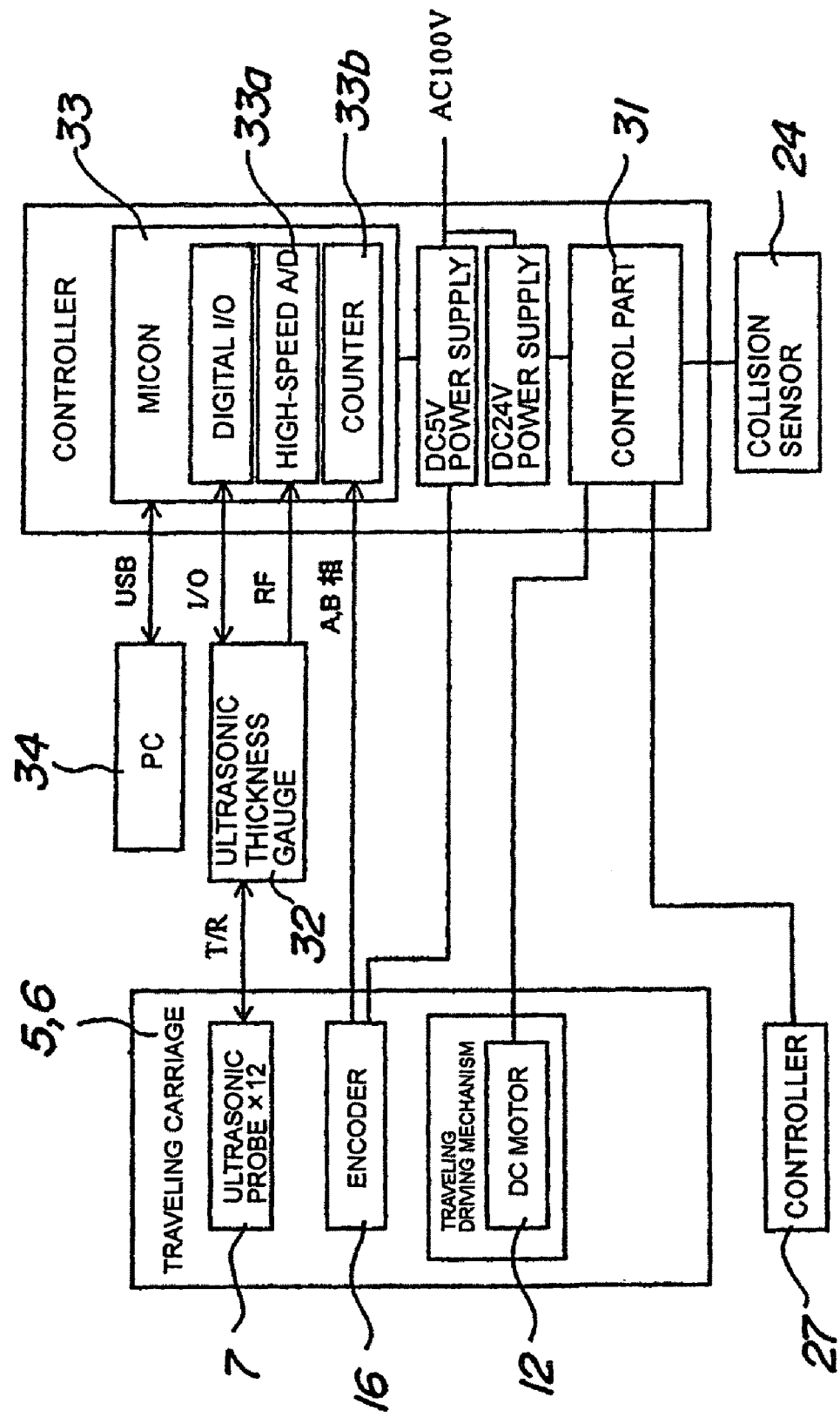
FIG. 16 is a block diagram showing a configuration of a control system.

By the configuration, the collision sensor 24 as obstruction detecting means detects obstructions in the traveling direction of the traveling carriage 5, the control part 31 shown in FIG. 16 drive controls the traveling motors 12 of the traveling carriage 5 to prevent the runaway and fall of the traveling carriage 5 based on the obstruction detection information, and informs the existence of obstruction by sounding an alarm or the like from a speaker 27*e* or emitting light from an LED (light emitting diode) 27*a* of a controller 27 shown in FIG. 15 as an example of informing means or the like.

Thus, even in the case where there are obstructions such as the agitator 2, agitating blades, the baffle 3 as a filing pipe also serving for accelerating agitation, a gas suction pipe, and a thermometer within the vessel on the vessel barrel part 1*b*, the steel plate thickness of the substantially entire surface of the vessel barrel part 1*b* can be measured by independently moving the left and right of the traveling carriage 5 forward/backward by the respective traveling motors 12 of four-wheel-drive as the traveling driving mechanism provided to the traveling carriage 5 and driving the traveling carriage 5 while avoiding the obstructions. However, the traveling driving mechanism may be formed by a caterpillar driving mechanism that can be independently moved forward/backward respectively on the left and right, a traveling driving mechanism such as a walking robot can be applied.

However, in the embodiment, the ultrasonic probe unit 13 is moved and projected toward the width direction of the traveling carriage 5 by rotationally operating the carriage member 15 by the rotative arm 22, however, a sliding mechanism is provided to the main frame of the traveling carriage 5, the carriage member 15 on which the ultrasonic probe unit 13 is mounted may be slidingly moved by electric operation or the like and projected toward the width direction of the traveling carriage 5.

When the carriage member 15 on which the ultrasonic probe unit 13 is mounted may be slidingly moved toward the width direction of the traveling carriage 5, the sliding mechanism may be arranged so as to be driven by carriage driving means such as a motor based on the obstruction detection information of the collision sensor 24 as obstruction detecting means, and the respective wheels of the small carriages 7*a* of the ultrasonic probe 7 may be casters that can independently turn around, or a lifting mechanism for lifting the carriage member 15 on which the ultrasonic probe unit 13 is mounted may be provided and once the carriage member 15 may be raised and slidingly moved toward the width direction of the traveling carriage 5, and then, lowered.

Further, by the buckles 28 as the attaching and detaching means, the common ultrasonic probe unit 13 on which plural ultrasonic probes 7 are mounted can be used by being selectively attached to the main body frame 14 of the traveling carriage 6 traveling on the vessel mirror part 1*a* and the carriage member 15 of the traveling carriage 5 traveling on the vessel barrel part 1*b*.

The controller 27 shown in FIG. 15 shows an example of the case where an inspector who has entered the reactor 1 from a manhole or the like operates, and a microphone 27*d* and the speaker 27*e* are used for communication with an inspector waiting outside of the reactor 1. 27*f* denotes a speed adjustment dial of the traveling carriage 5, and 27*g* denotes a speed balance adjustment dial for fine adjustment of the speed balance of the left and right wheels of the traveling carriage 5.

Further, 27*h* denotes direction reversing buttons for switching forward/backward direction of the traveling carriage 5. Remote operation can be made easier by switching the direction reversing buttons 27*h* in response to the orientation of front and rear of the traveling carriage 5 opposed to the operating inspector to reverse the operation of the left and right wheel operation sticks 27*b* and 27*c*.

27*i* denotes a traveling start button for starting the traveling of the traveling carriage 5, and 27*j* denotes a traveling stop button for stopping the traveling of the traveling carriage 5. Further, the traveling movement of the traveling carriage 6 traveling on the vessel mirror part 1*a* can be also operated using the controller 27 shown in FIG. 15.

Next, using FIG. 16, signal processing during thickness measurement will be described. First, pulse voltages are periodically sent from an ultrasonic thickness gauge 32 to the ultrasonic probe 7 to allow a transmission transducer T of the ultrasonic probe 7 to oscillate, and generated ultrasonic waves are sent into a steel plate as an object to be inspected.

Reflection waves from the bottom surface of the object are received by a reception transducer R of the ultrasonic probe 7, and a voltage obtained by the oscillation of the reception transducer R is amplified by the ultrasonic thickness gauge 32 and output to a high-speed analog/digital converter (hereinafter, simply referred to as "high-speed A/D") 33a of a microcomputer (hereinafter, referred to as "micon") 33.

In the micon 33, a digital converted value of waveform obtained by the high-speed A/D 33a is transmitted to the PC 34 with traveling position information of the traveling carriages 5 and 6 by the encoder 16 obtained via a counter 33b.

In the PC 34, the thickness of the object is calculated using a sound speed of the object, which has been obtained in advance, based on the digital converted value of waveform obtained by the high-speed A/D 33a.

The above processing is performed with respect to the twelve ultrasonic probes 7 (12 ch (channels) of combinations of pairs of transmission oscillators T and reception oscillators R) in order, and thickness measurement is continuously performed. For example, assuming that the period of the pulse voltage sent from the ultrasonic thickness gauge 32 to the ultrasonic probe 7 is 12 kHz, the measurement is performed with 1 kHz per 1 ch.

On the display screen of the PC 34, thickness information currently measured is displayed with the traveling position information of the traveling carriages 5 and 6 in real time by a measurement screen 35 shown in FIG. 20. At the end of the measurement, a save and end button 35c on the measurement screen 35 is clicked to save the measurement data in a file.

Figure 17:
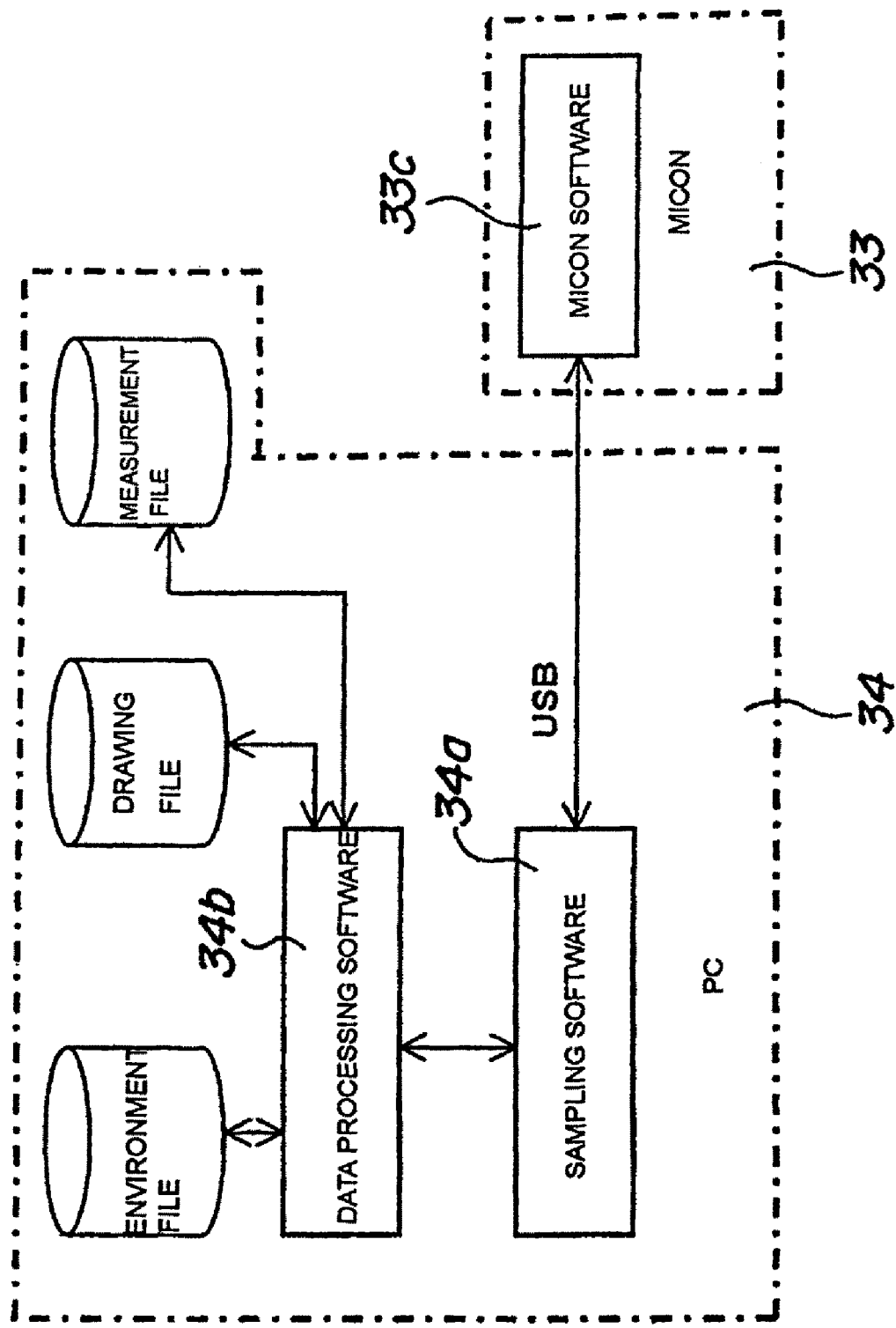
FIG. 17 is a block diagram showing a configuration of an information processing system for performing processing of thickness measurement data.

Next, using FIG. 17, a software configuration of the thickness measuring device will be described. Micon software 33c shown in FIG. 17 acquires data such as ch identifying signals, length measurement data (encoder counts), and ultrasonic full-wave type digital values (40 MHz×2048 points, 151 mm) by synchronization signals (1 kHz/ch, total 12 kHz) from the ultrasonic thickness gauge 32, and transmits the data to the PC 34. Further, the micon software 33c performs control of an ultrasonic flaw detector.

Sampling software 34a for capturing thickness data performs communication with the micon 33 and processes the captured ultrasonic full-wave type digital values to detect peaks. FIG. 20 shows an example of the measurement screen 35 of the sampling software 34a during measurement. The control of the ultrasonic thickness gauge 32, setting and acquisition of sampling conditions, capture of measurement data, etc. are executed in response to the instructions from data processing software 34b.

Figure 21:
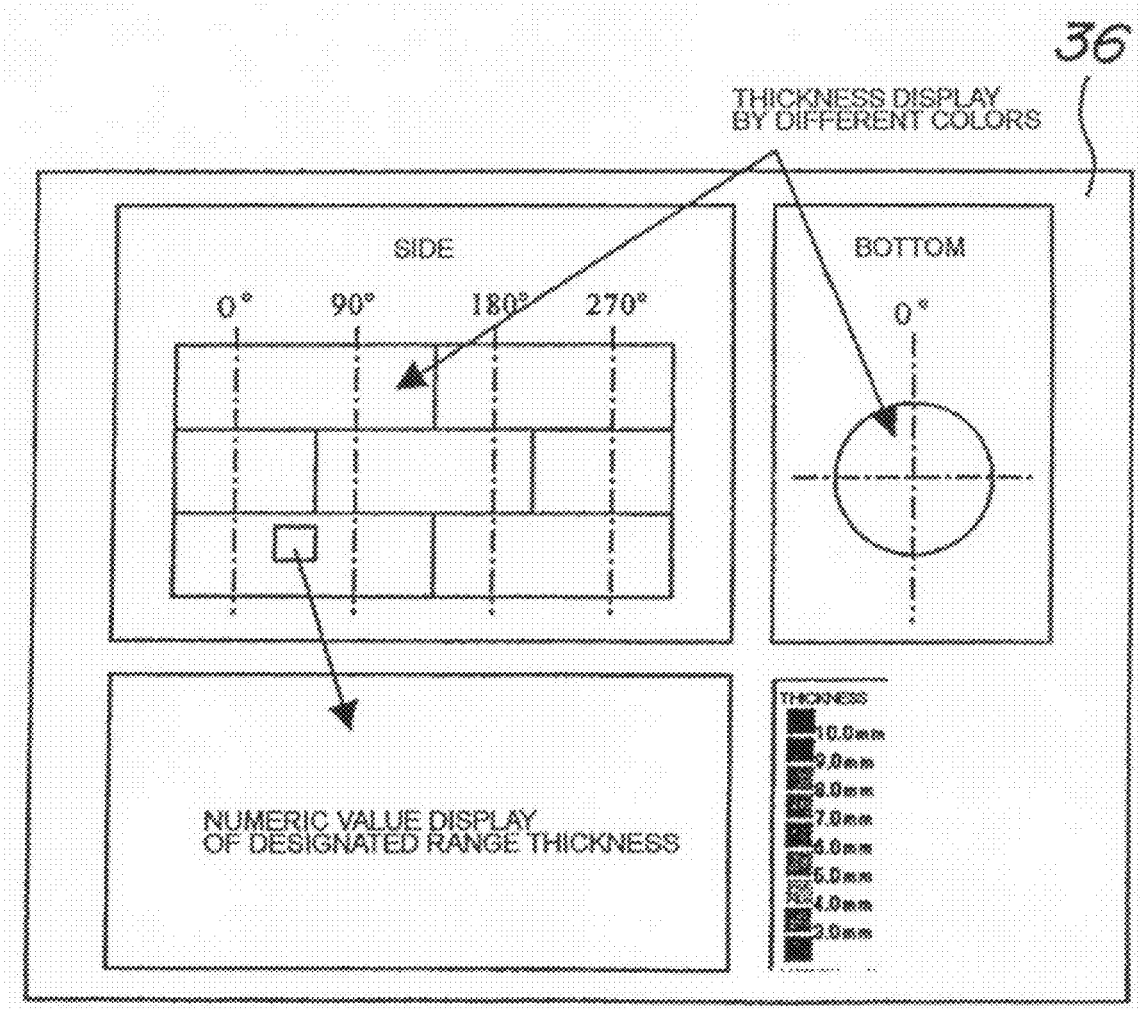
FIG. 21 shows an example of a thickness distribution chart of data processing software.
Figure 23:
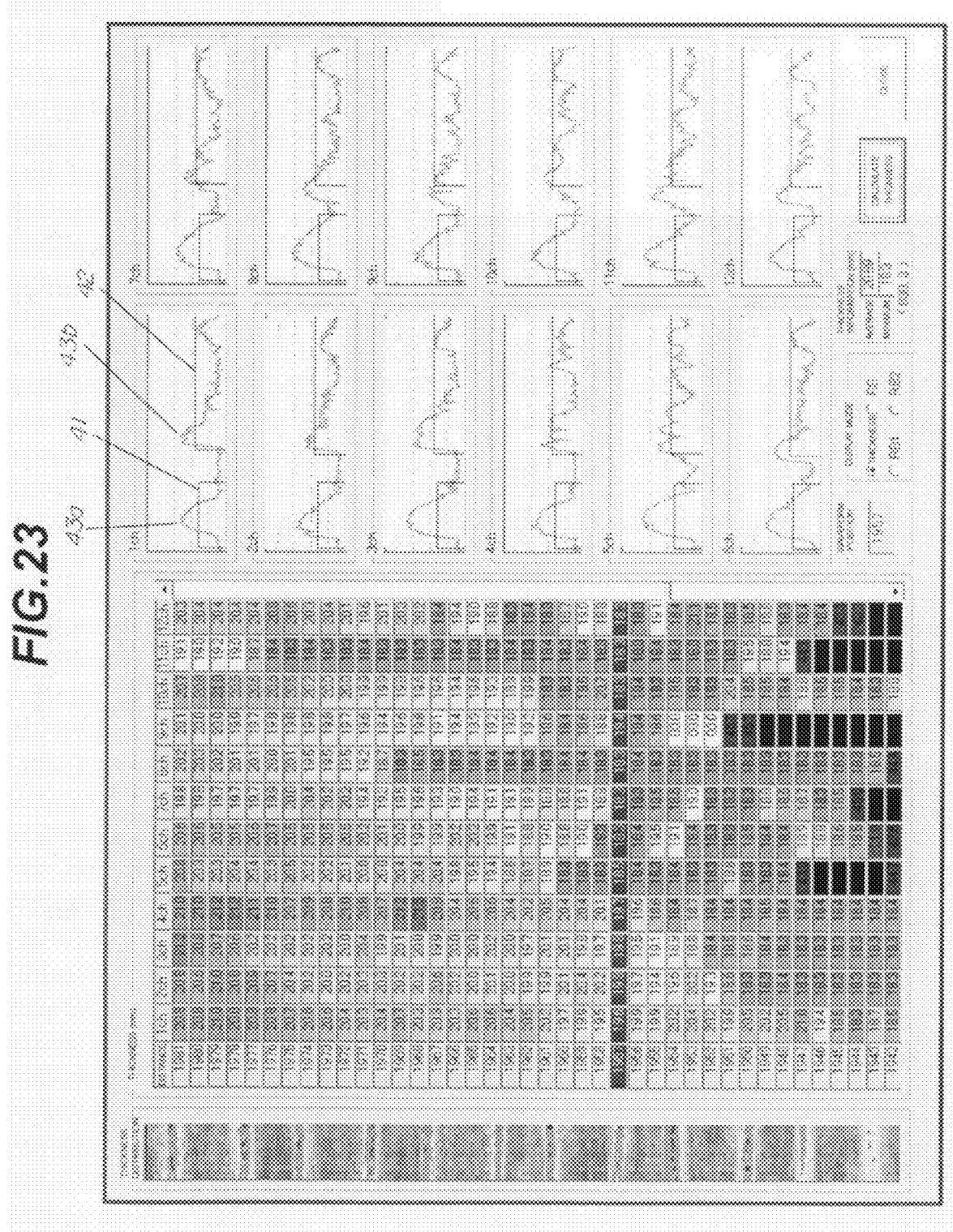
FIG. 23 is an explanatory diagram of a problem of a conventional example in which a bottom surface echo monitoring gate is fixed.

The data processing software 34b for forming thickness images as shown in FIGS. 21 and 22 performs condition settings of the ultrasonic thickness gauge 32, correction (obtainment of sound speed of the object), creation of drawing and measurement of the reactor 1, creation, display, and printing of a thickness distribution chart (distinguished using different colors) of the reactor 1, etc.

Figure 18:
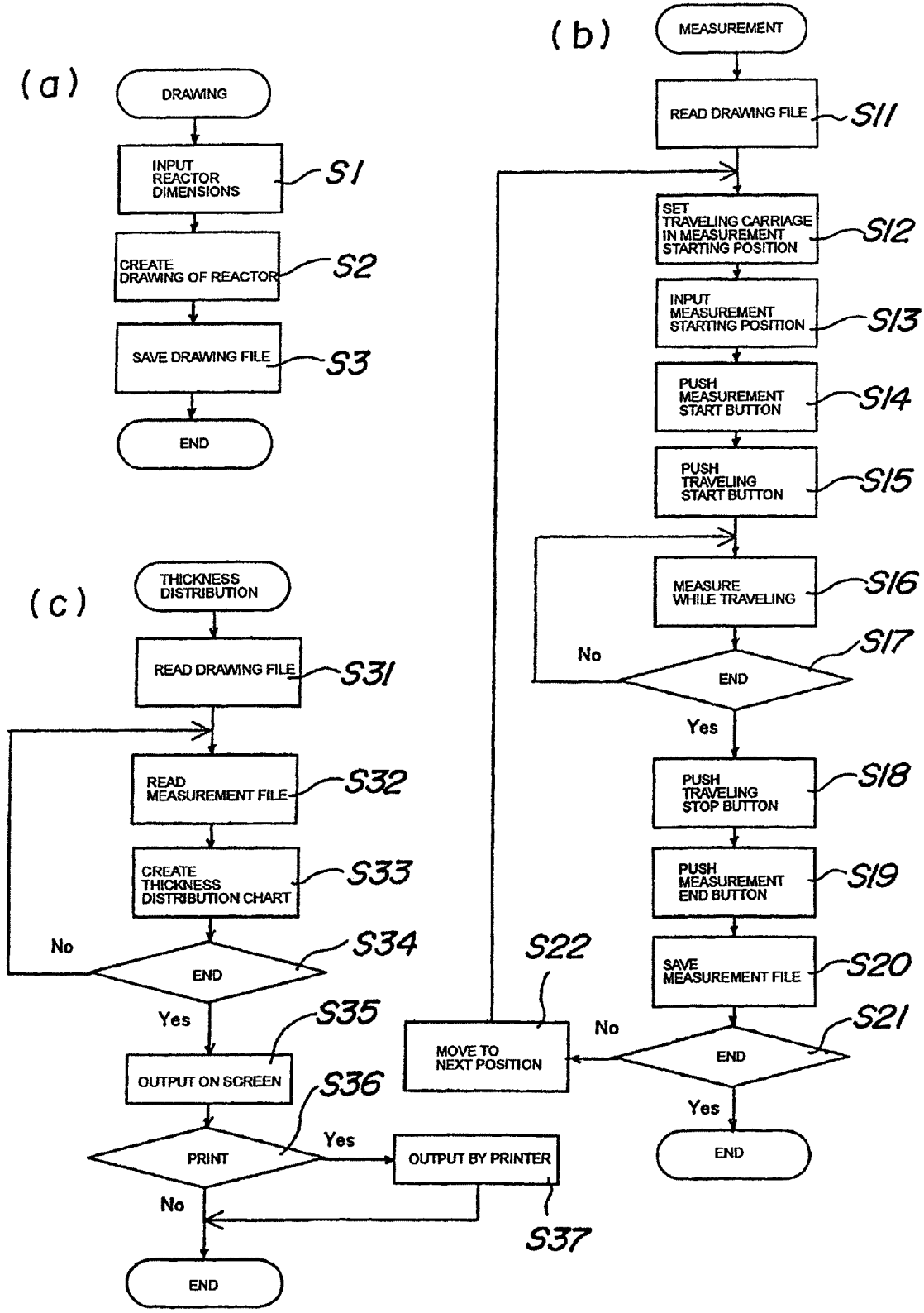
FIG. 18 are flowcharts showing a state of performing processing of thickness measurement data.

Next, the data processing operation executed by the data processing software 34b will be described according to FIG. 18. FIG. 18(a) shows an operation of creating a drawing of the reactor 1. At step S1, when dimensions of the reactor 1 are input using input means such as a keyboard or mouse of the PC 34, the drawing of the reactor 1 is created by the data processing software 34b (step S2), and a file of the created drawing is saved (step S3).

FIG. 18(b) shows an operation of performing thickness measurement. The file of the created drawing saved at the step S3 is read in (step S11), and the traveling carriages 5 and 6 are set in measurement starting positions (step S12). The measurement starting positions are input using input means such as a keyboard or mouse of the PC 34 (step S13), a measurement start button 35a of the measurement screen 35 shown in FIG. 20 displayed on the display screen of the PC 34 is clicked (step S14), and the traveling start button 27j of the controller 27 shown in FIG. 15 is pushed (step S15).

The traveling of the traveling carriages 5 and 6 measure the thickness of the vessel steel plate by the ultrasonic probes 7 while traveling (step S16). In the case of the traveling carriage 6 for measuring the thickness of the vessel mirror part 1a of the reactor 1, at the stage where a lap with the radius of curvature regulated by the turning radius regulating member 19 is finished, or, in the case where the vessel barrel part 1b is vertically measured by the traveling carriage 5 for measuring the thickness of the vessel barrel part 1b of the reactor 1, at the stage where a linear line is finished, or, in the case where the vessel barrel part 1b is circumferentially measured by the traveling carriage 5, at the stage where a lap of the vessel barrel part 1b of the reactor 1 is finished (step S17), the traveling stop button 27j of the controller 27 shown in FIG. 15 is pushed, respectively (step S18), a measurement pause button 35b of the measurement screen 35 shown in FIG. 20 displayed on the display screen of the PC 34 is clicked (step S19), the save and end button 35c on the same measurement screen 35 is clicked to save the thickness measurement data associated with the traveling position information of the traveling carriages 5 and 6 detected by the encoder 16 in a file (step S20).

Then, until the thickness measurement of all regions of the vessel mirror part 1a and vessel barrel part 1b of the reactor 1 are finished (step S21), the carriages are moved to the next thickness measurement positions in order (step S22), and the thickness measurement is ended at the stage where the thickness measurement of all regions of the vessel mirror part 1a and vessel barrel part 1b of the reactor 1 are finished.

FIG. 18(c) shows the operation of creating a distribution chart of the measured thickness. The file of the created drawing saved at the step S3 is read in (step S31), and the thickness measurement file saved at the step S20 is read in (step S32).

Then, the data processing software 34b creates the measured thickness distribution chart as shown in a thickness distribution chart screen 36 in FIG. 21 by associating the created drawing data and thickness measurement data of the reactor 1 (step S33). At the stage where the creation of the thickness distribution chart is finished (step S34), the thickness distribution chart screen 36 shown in FIG. 21 is output (step S35), when printing (step S36), output by a printer (step S37), and the process is ended.

FIG. 22 shows an example of a result of thickness measurement. FIG. 22(a) is a display of corroded portions of the vessel steel plate of the reactor 1, FIG. 22(b) is a display of the thickness distribution chart distinguished by different colors, and FIG. 22(c) is a display of measured numeric values of thickness with respect to each unit cell of 5 mm×5 mm.

Figure 19:
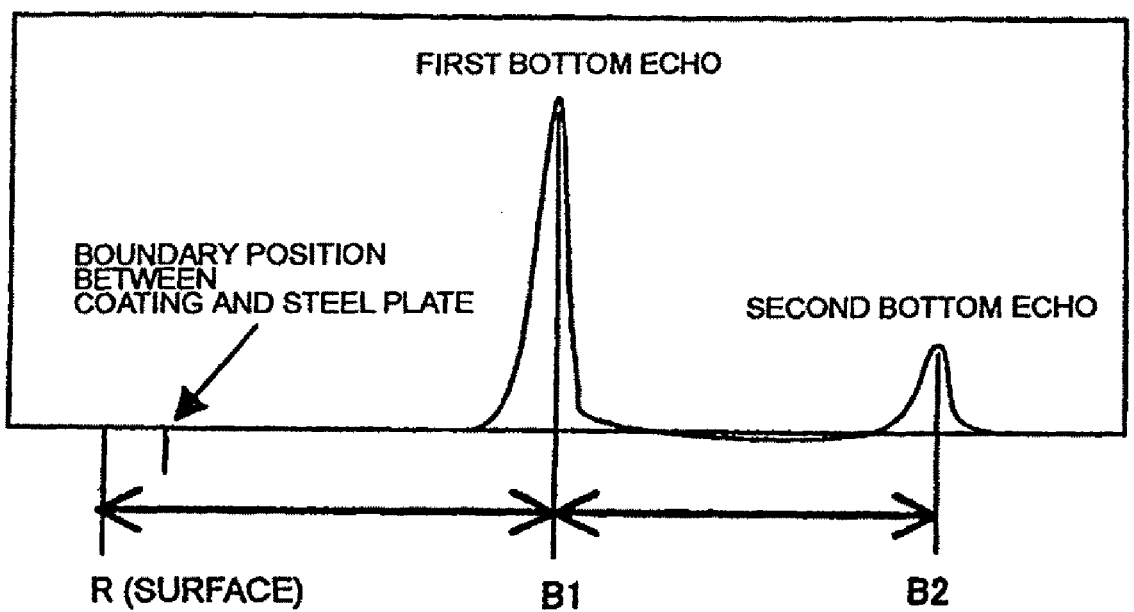
FIG. 19 is an explanatory diagram of an example of a thickness measuring method.

Normally, a coating is applied on the surface of the steel plate for corrosion control, and the value obtained by subtracting the thickness of the coating is the real thickness. Accordingly, in the embodiment, when the thickness of vessel steel plate is measured by the ultrasonic proves 7 disposed on the surface of the coating surface, based on the peak positions detected from the ultrasonic full-wave type digital values, as shown in FIG. 19, the real thickness of steel plate tR·B2 can be obtained from the difference between the total thickness tR·B1 including the coating based on the bottom surface echoes obtained by receiving ultrasonic waves oscillated from the transmission oscillators T of the ultrasonic probes 7 disposed on the surface of the coating surface and reflected at the bottom surface of the steel plate for the first time by the reception oscillator R and the total thickness tR·B2 including the coating based on the bottom surface echoes obtained by receiving ultrasonic waves oscillated from the transmission oscillators T of the ultrasonic probes 7 disposed on the surface of the coating surface, reflected at the boundary surface of the coating and the steel plate, and further reflected at the bottom surface of the steel plate for the second time by the reception oscillator R.

Here, in the case where, although the signal of the bottom surface echo received for the first time, the signal of the bottom surface echo received for the second time is so small that the thickness tB·B2 can not be acquired, the thickness tB1·B2 is obtained using position data obtained in the vicinity thereof.

That is, assuming that the predicted value of thickness in a position where the signal of the bottom surface echo received for the second time is so small that the thickness tB1·B2 can not be acquired is t cur, the total thickness including the coating thickness in the position where the thickness tB1·B2 can not be acquired is t(R·B1)cur, the total thickness including the coating thickness in a position where the thickness tB1·B2 can be acquired in the vicinity is t(R·B1)near, and the thickness in the position where the thickness tB1·B2 can be acquired in the vicinity is t(B1·B2)near, the predicted value of thickness can be calculated by tcur=t(R·B1)cur−{t(R·B1)near−t(B1·B2)near}, and this value can be adopted as the thickness.

However, in the above embodiment, the example of vessel in the case where the vessel barrel 1b substantially in the cylindrical form is provided along the vertical direction and the vessel mirror part 1a is provided at the top and bottom has been described, however, the embodiment can be similarly applied to the vessel in the case where the vessel barrel 1b substantially in the cylindrical form is provided along the horizontal direction and the vessel mirror part 1a is provided on the left and right.

Next, using FIGS. 25 to 27, a thickness measuring method according to the invention will be described. In the embodiment, the thicknesses of the vessel mirror part 1a and vessel barrel part 1b of the reactor 1 as a vessel are continuously measured by detecting echo height voltage values of an ultrasonic response waveform using the ultrasonic probes 7 mounted on the traveling carriages 5 and 6.

Figure 26:
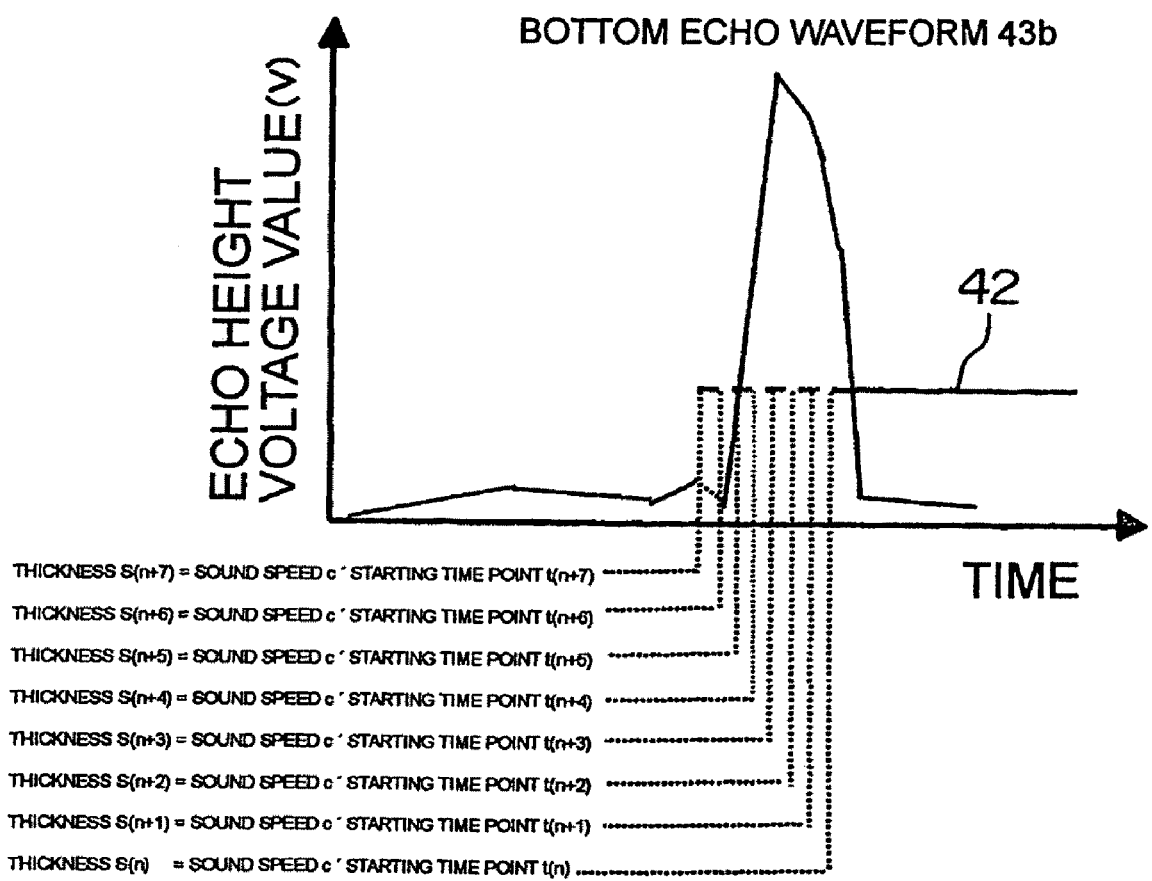
FIG. 26 shows a state of sequentially moving the starting time point of the bottom surface echo monitoring gate to approximate it to the rising time point of the ultrasonic response waveform by the ultrasonic probes at the bottom surface of the vessel steel plate.

As shown in FIG. 26, a bottom surface echo monitoring gate 42 for detecting echo height voltage values of the bottom surface echo waveform 43b as an ultrasonic response waveform by the ultrasonic probes 7 at the bottom surface of the vessel steel plate is set in a predetermined duration range, the first thickness S(n) of the vessel steel plate calculated in a position where, assuming that the starting time point of the bottom surface echo monitoring gate 42 is the first starting time point t(n), the bottom surface echo monitoring gate 42 cuts the bottom surface echo waveform 43b and the second thickness S(n+1) of the vessel steel plate calculated in a position where, when the starting time point of the bottom surface echo monitoring gate 42 is moved to the second starting time point t(n+1) that is predetermined time earlier than the first starting time point t(n), the bottom surface echo monitoring gate 42 cuts the bottom surface echo waveform 43b are compared, and, if the second thickness S(n+1) is smaller than the first thickness S(n), the starting time point of the bottom surface echo monitoring gate 42 is moved to a response time that is predetermined time earlier.

In FIG. 26, when the starting time point of the bottom surface echo monitoring gate 42 is sequentially moved to t(n)→t(n+1)→t(n+2)→t(n+3)→t(n+4)→t(n+5)→t(n+6)→t(n+7), the thicknesses of the vessel steel plate calculated in positions where the bottom surface echo monitoring gate 42 cuts the bottom surface echo waveform 43b are S(n)>S(n+1)>S(n+2)>S(n+3)>S(n+4)>S(n+5)>S(n+6)=S(n+7).

Then, if the second thickness S(n+7) and the first thickness S(n+6) are equal, the starting time point t(n+6) of the bottom surface echo monitoring gate 42 is fixed.

Figure 25:
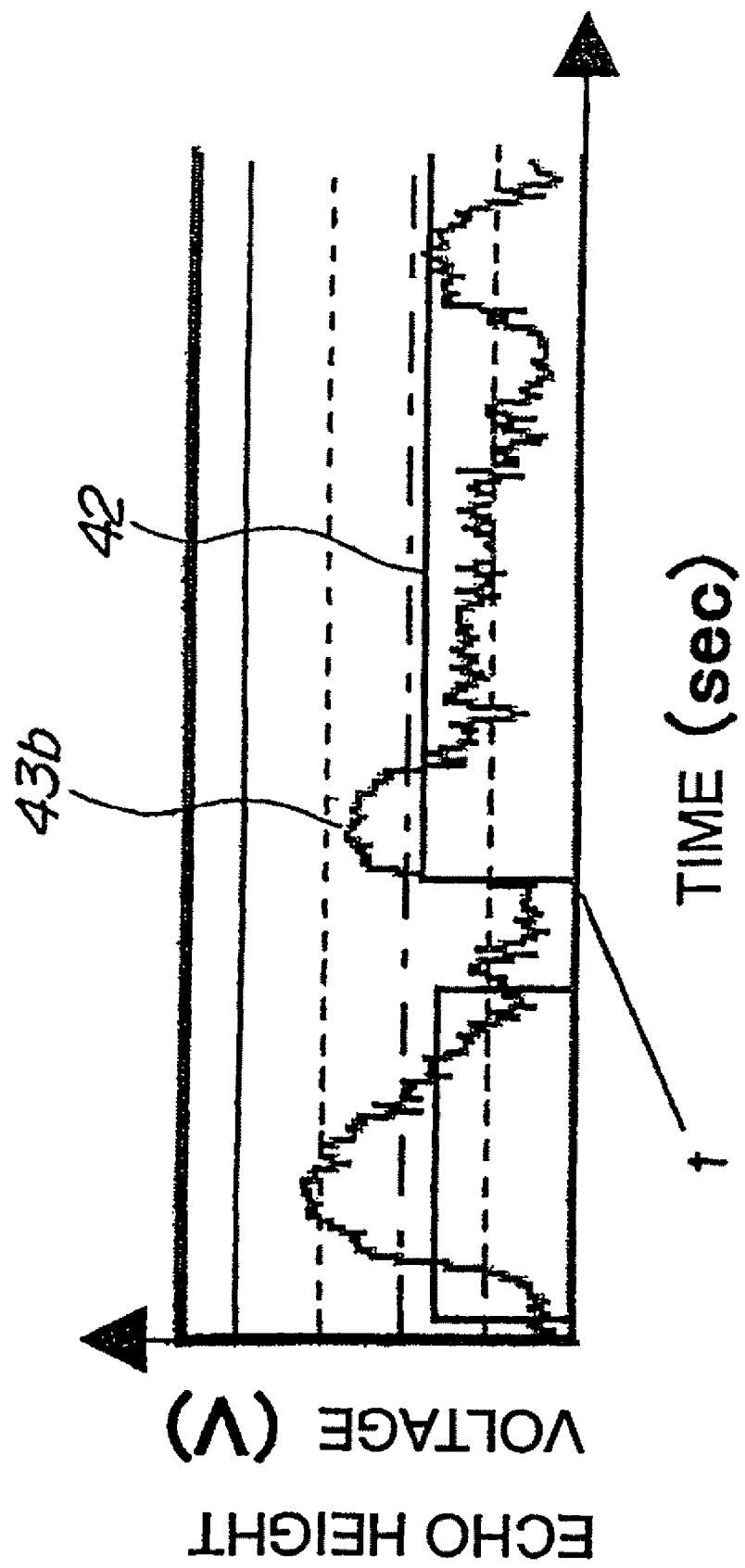
FIG. 25 shows a state in which thicknesses are measured by moving the starting time point of the bottom surface echo monitoring gate to approximate it to the rising time point of the ultrasonic response waveform by the ultrasonic probes at the bottom surface of the vessel steel plate.

Thereby, as shown in FIG. 25, the starting time point t of the bottom surface echo monitoring gate 42 can be approximated to the rising time point of the bottom surface echo waveform 43b as the ultrasonic response waveform by the ultrasonic probes at the bottom surface of the vessel steel plate. As shown in FIG. 26, since the starting time point t(n+6) of the bottom surface echo monitoring gate 42 is fixed if the second thickness S(n+7) and the first thickness S(n+6) are equal, the thickness S of the vessel steel plate calculated in the position where the bottom surface echo monitoring gate 42 cuts the bottom surface echo waveform 43b can be measured accurately.

However, there is no problem that the starting time point t of the bottom surface echo monitoring gate 42 is moved to t(n+7), if there is no flaw echo waveform, multiple echo waveform, or the like before the bottom surface echo waveform 43b as shown in FIG. 26, however, if a flaw echo waveform or multiple echo waveform (not shown) exists before the bottom surface echo waveform 43b, the bottom surface echo monitoring gate 42 detects the flaw echo waveform or multiple echo waveform. Accordingly, by fixing the starting time point t(n+6) of the bottom surface echo monitoring gate 42, even if a flaw echo waveform, multiple echo waveform, or the like (not shown) exists before the bottom surface echo waveform 43b, the bottom surface echo monitoring gate 42 never detects the flaw echo waveform, multiple echo waveform, or the like.

When the starting time point t of the bottom surface echo monitoring gate 42 is moved to a response time that is predetermined time earlier, the time pitch of half-wave length of the period of vibration of the ultrasonic probes 7 can be made into the minimum unit. For example, when the vibration frequency of the ultrasonic probe 7 is 5 MHz, the time of half-wave length is $0.1 \times 10^{-6}$ [sec], the starting time point of the bottom surface echo monitoring gate 42 can be sequentially moved to earlier response time with the time pitch as the minimum unit.

Figure 24:
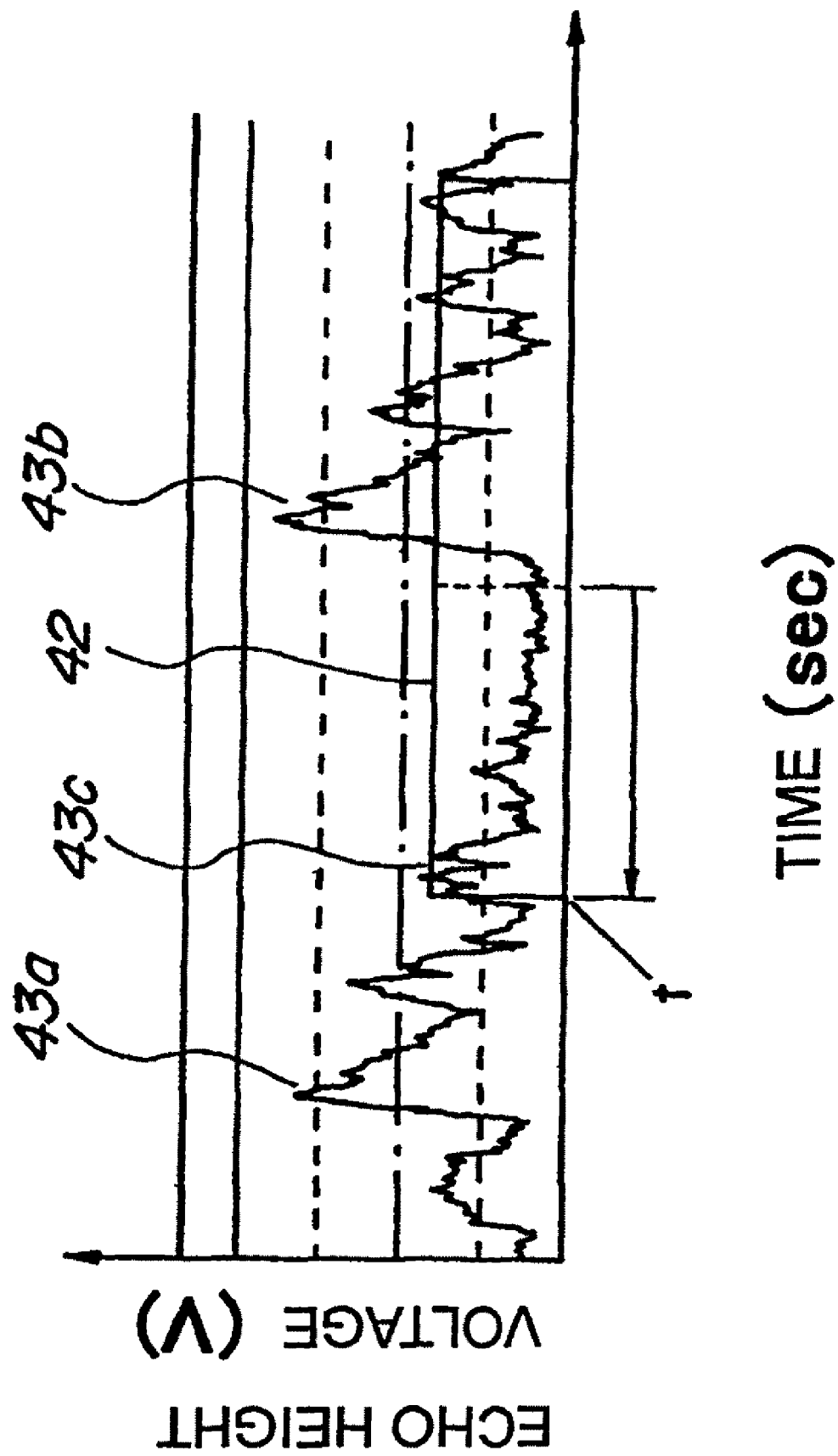
FIG. 24 is an explanatory diagram of a problem of a conventional example in which a range of the bottom surface echo monitoring gate is extended.

Thereby, as described shown in FIG. 24, by not broadening the monitoring range of the bottom surface echo monitoring gate 42 carelessly, but providing a narrow monitoring range of the bottom surface echo monitoring gate 42, the correct thickness of steel plate can be obtained without erroneous detection of noise such as the multiple echo waveform 43.

Figure 27:
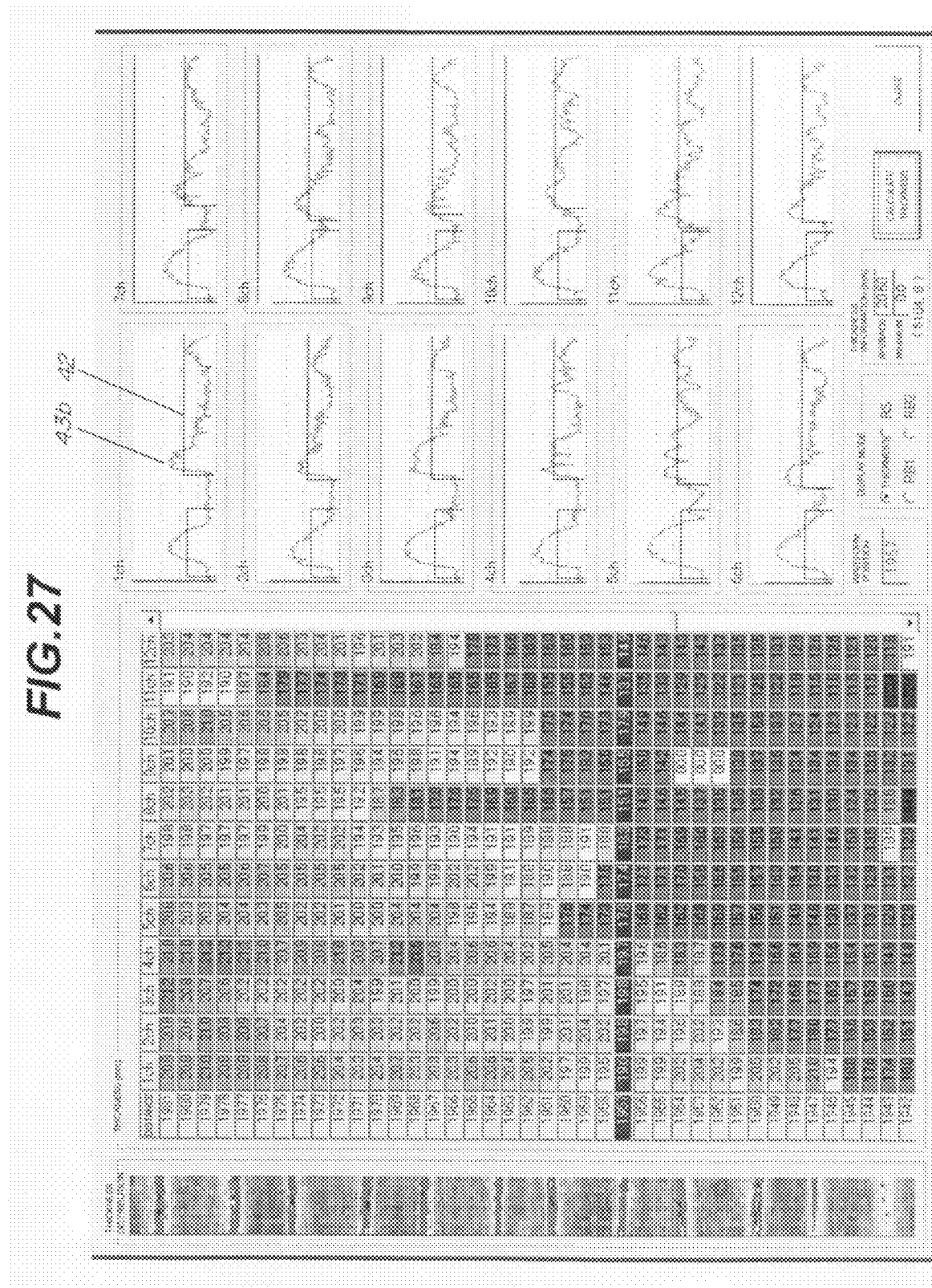
FIG. 27 shows an state in which the thicknesses are measured by moving the starting time points of the respective bottom surface echo monitoring gates of 1 ch to 12 ch, respectively, to approximate them to the rising time points of the ultrasonic response waveforms by the ultrasonic probes at the bottom surface of the vessel steel plate according to the thickness measuring method of the invention.

FIG. 27 shows an example in which the respective bottom surface echo monitoring gates 42 are moved in all channels of ch1 to ch12 of the respective ultrasonic probes 7, the starting time points t of the bottom surface echo monitoring gates 42 are fixed close to the rising time point of the bottom surface echo waveforms 43b as ultrasonic response waveforms by the ultrasonic probes 7 at the bottom surface of the vessel steel plate, and thereby, no overlooking of the bottom surface echo waveforms 43b occur in all channels.

Thus, in the multichannel thickness measuring device for continuously measuring thicknesses of a vessel steel plate using ultrasonic probes 7, the starting time point t of the monitoring range of each bottom surface echo monitoring gate 42 set for detecting each bottom surface echo waveform 43b reflected and returned from the bottom of the steel plate can be automatically set with respect to each channel.

Next, using FIGS. 28 to 30, a noise determining method in the case where there is a separation between the vessel steel plate and the surface layer of a vessel steel plate formed by bonding surface layers made of different materials will be described.

FIG. 28 show ultrasonic response waveforms by the ultrasonic probes at the boundary surface between the surface layer and the vessel steel plate. FIG. 28(a) shows an example of the ultrasonic response waveform in the case where there is a separation between the vessel steel plate and the surface layer, FIG. 28(b) shows an example of the ultrasonic response waveform having a sound part and a reduced thickness part in the case where there is no separation between the vessel steel plate and the surface layer, and FIG. 28(c) shows an example of the ultrasonic response waveform in the case where there is a flaw such as an inclusion or lamination in the vessel steel plate.

In the embodiment, when the thicknesses of a vessel steel plate formed by bonding surface layers made of different materials are continuously measured by detecting echo height voltage values of an ultrasonic response waveform using the ultrasonic probes 7 from the surface layer side of the vessel steel plate, as shown in FIG. 28, a boundary surface echo monitoring gate 41 for detecting echo height voltage values of a boundary surface reflection echo waveform 43a as the ultrasonic response waveform by the ultrasonic probes 7 at the boundary surface between the surface layer and the vessel steel plate are set in a predetermined duration range.

Then, at least one of average echo height voltage values, echo height accumulated voltage values, and echo height peak voltage values in the duration range of the boundary surface echo monitoring gate 41 are calculated, and thereby, a statistical distribution in the entire vessel is created.

FIG. 29(a) shows a statistical distribution in the entire vessel created by calculating average echo height voltage values in the duration range of the boundary surface echo monitoring gate 41, in the case where a separation is produced between the vessel steel plate formed by bonding surface layers made of different materials and the surface layer, as shown in FIG. 28(a), a separation waveform of high echo height voltage values appears as the boundary surface echo waveform 43a, and the no-separation distribution formed by the normal boundary surface echo waveform 43a shown in FIG. 28(b) and the separation distribution formed by the separation waveform shown in FIG. 28(a) are dichotomized in the statistical distribution.

Then, the separation distribution with higher echo height voltage values, which has been dichotomized from the statistical distribution, is determined as a noise group due to separation between the vessel steel plate the surface layer.

FIG. 29(b) shows a statistical distribution in the entire vessel created by calculating accumulated echo height voltage values in the duration range of the boundary surface echo monitoring gate 41, and the statistical distribution is dichotomized into the no-separation distribution as shown in FIG. 28(b) and the separation distribution shown in FIG. 28(a). Then, the separation distribution with higher echo height accumulated values, which has been dichotomized from the statistical distribution, is determined as a noise group due to separation between the vessel steel plate the surface layer.

FIG. 29(c) shows a statistical distribution in the entire vessel created by calculating peak echo height voltage values in the duration range of the boundary surface echo monitoring gate 41, and the statistical distribution is dichotomized into the no-separation distribution as shown in FIG. 28(b) and the separation distribution shown in FIG. 28(a). Then, the separation distribution with higher echo height peak values, which has been dichotomized from the statistical distribution, is determined as a noise group due to separation between the vessel steel plate the surface layer.

Figure 29:
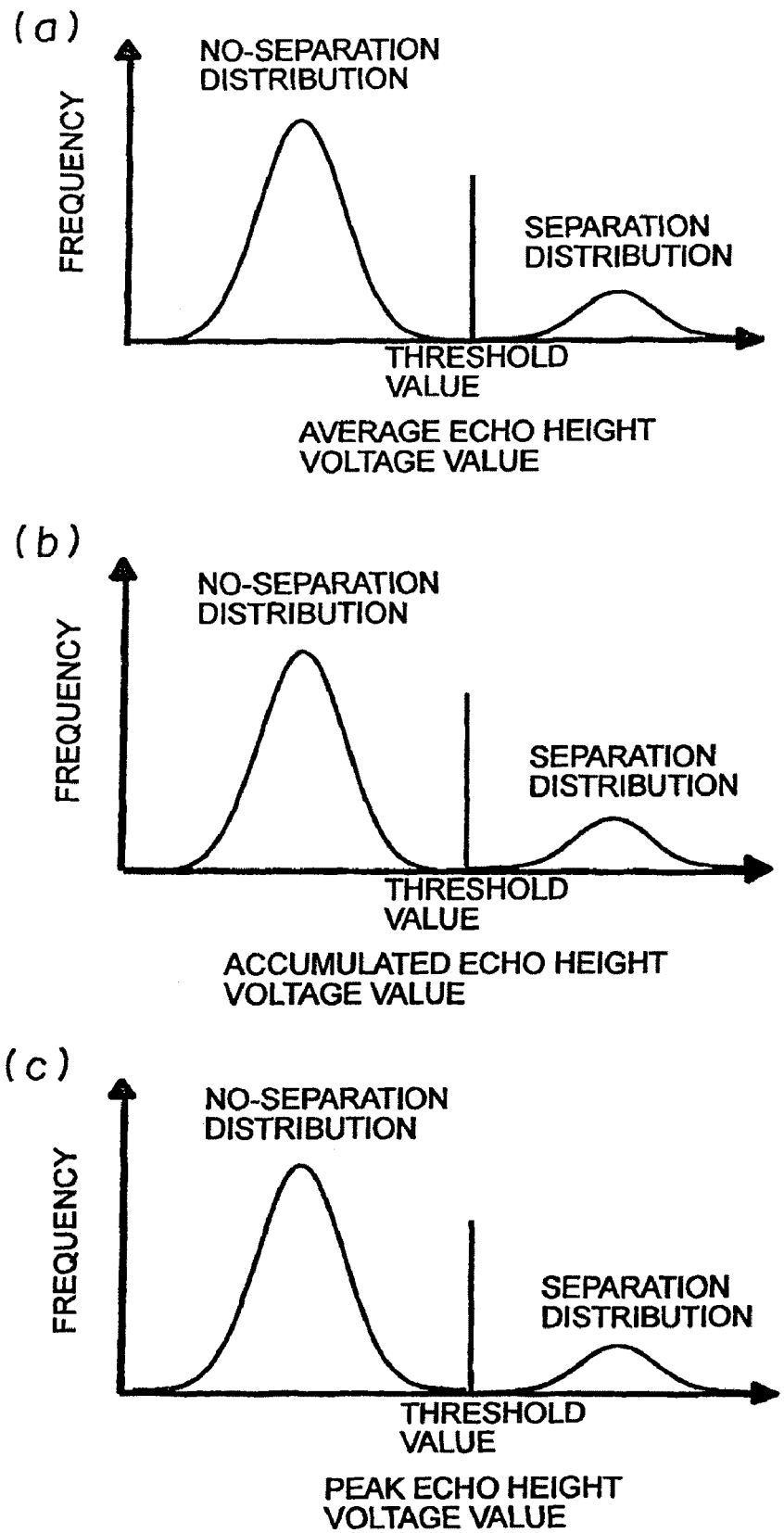
FIGS. 29(a) to 29(c) show states in which, as a result of generating statistical distributions in the entire vessel by respectively calculating average echo height voltage values, accumulated echo height voltage values, and peak echo height voltage values in the duration range in which the boundary surface echo monitoring gate has been set, they are dichotomized into no-separation distributions and separation distributions.
Figure 30:
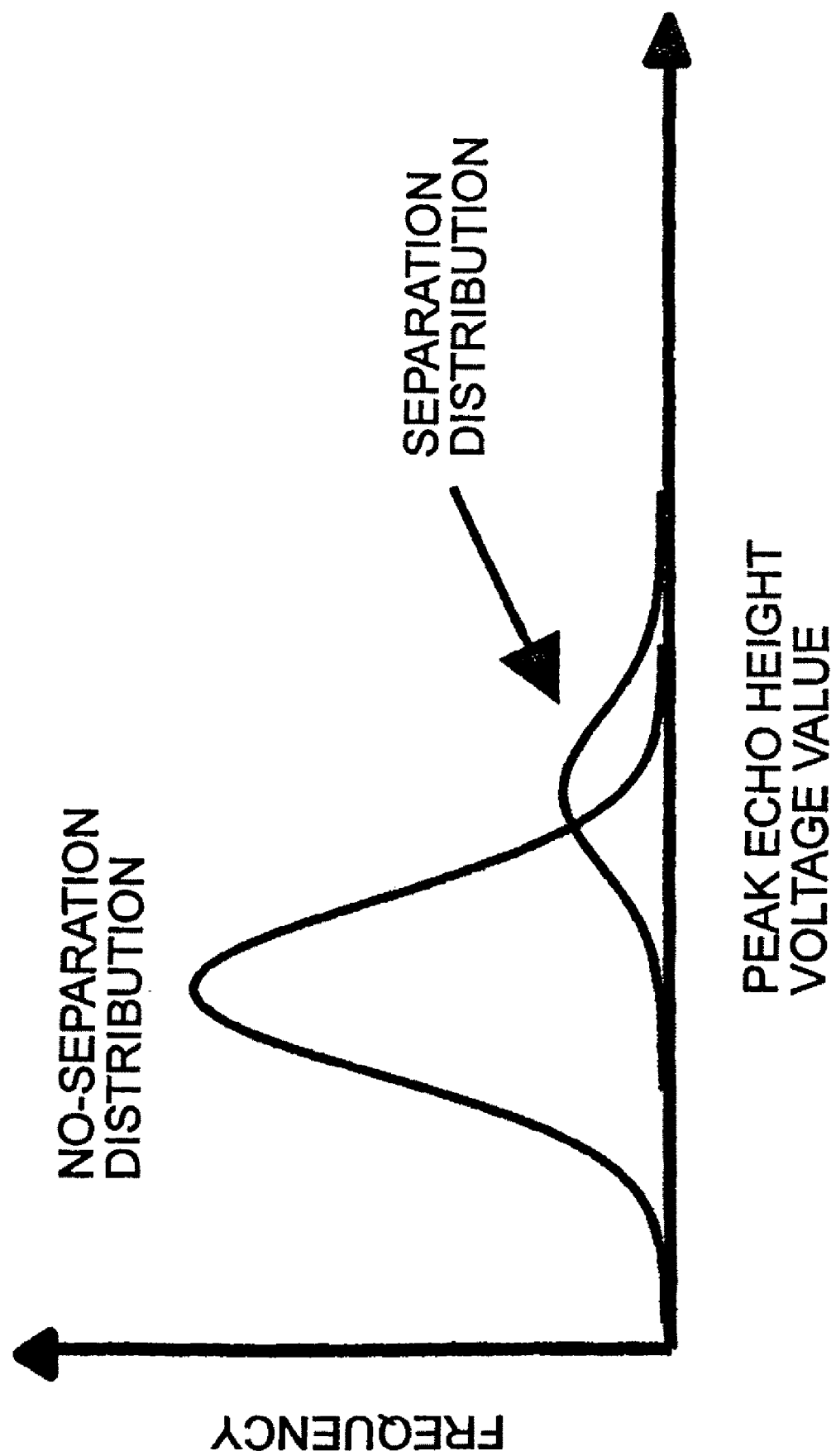
FIG. 30 shows an example in the case where, as a result of creating a statistical distribution in the entire vessel by calculating peak echo height voltage values in the duration range in which the boundary surface echo monitoring gate has been set, the no-separation distribution and the separation distribution are superimposed, and therefore, they can not be dichotomized easily.

FIG. 30 shows an example in the case where, as a result of creating a statistical distribution in the entire vessel by calculating peak echo height voltage values in the duration range in which the boundary surface echo monitoring gate 41 has been set, the no-separation distribution and the separation distribution are superimposed, and therefore, they can not be dichotomized easily. In this case, using in combination with the statistical distribution of average echo height voltage values in the entire vessel or the statistical distribution of accumulated echo height voltage values in the entire vessel shown in FIG. 29, the separation distribution dichotomized from the statistical distributions can be determined as a noise group.

That is, using at least two of the statistical distribution of average echo height voltage values in the entire vessel, the statistical distribution of accumulated echo height voltage values in the entire vessel, and the statistical distribution of peak echo height voltage values in the entire vessel shown in FIG. 29, the separation distribution dichotomized from the statistical distributions can be determined as a noise group, and thereby, determination accuracy of noise group can be improved.

Further, since thickness is not displayed by designating the noise groups of the separation distributions dichotomized from the respective statistical distributions, erroneous display showing thinner thicknesses than real thicknesses due to separation between the vessel steel plate the surface layer can be prevented.

Next, using FIGS. 31 to 33, a noise determining method in the case where there is an inclusion, lamination, or the like in the vessel steel plate will be described.

Figure 32:
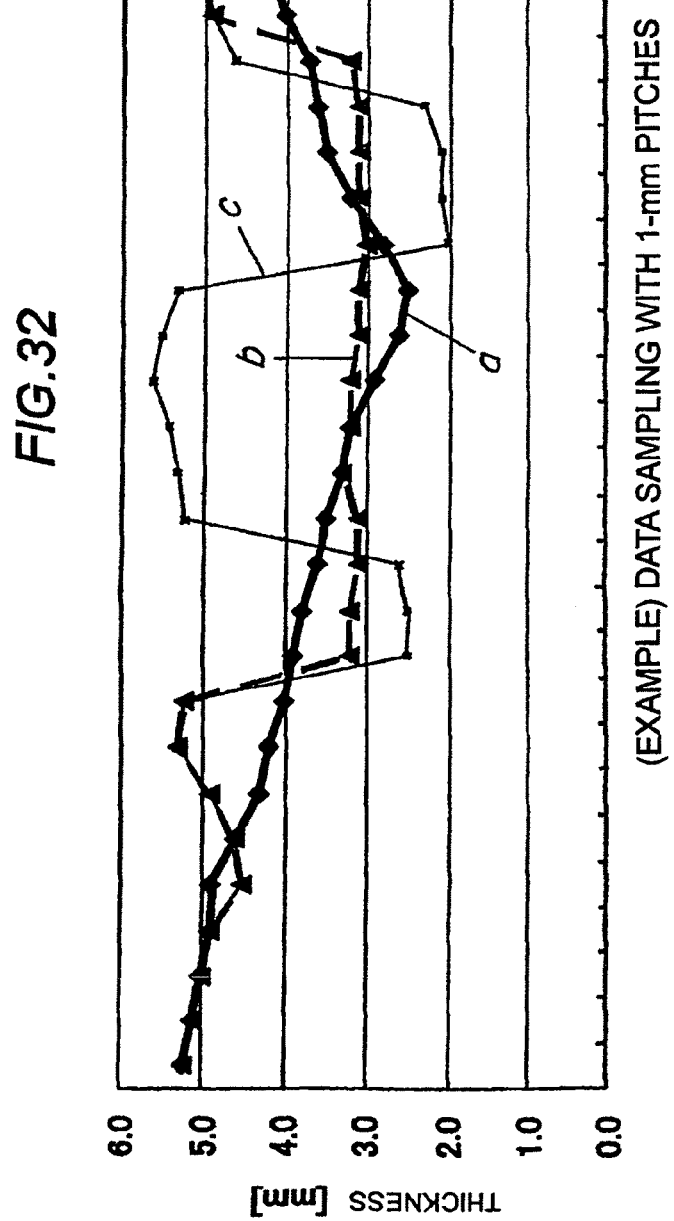
FIG. 32 shows states in which the thickness of the vessel steel plate measured using ultrasonic probes with 1-mm pitches changes, respectively, in the cases where the steel plate has a reduce thickness due to corrosion, there is a lamination, and there is an inclusion.

A curve a shown in FIG. 32 shows a state in which the thickness changes when the thickness of the part with reduced thickness due to corrosion of the vessel steel plate is measured using ultrasonic probes 7 with 1-mm pitches, a curve b shows a state in which the thickness changes when the thickness of the part with a lamination existing in the vessel steel plate is measured using ultrasonic probes 7 with 1-mm pitches, and a curve c shows a state in which the thickness changes when the thickness of the part with an inclusion existing in the vessel steel plate is measured using ultrasonic probes 7 with 1-mm pitches.

As shown by the curve a in FIG. 32, the thickness of the part with a reduced thickness due to corrosion of the vessel steel plate changes slowly, however, as shown by the curves b and c, the thickness of the part with a lamination or inclusion existing in the vessel steel plate changes suddenly at the both ends of the part of the lamination or inclusion.

For example, if the measured thickness of the steel plate abnormally changes by 5 mm as the positions of the ultrasonic probes 7 are shifted just 1 mm, that is not considered as data change due to corrosion, and the measured thickness data can be separated and removed as a noise.

In the case the thicknesses of a vessel steel plate are continuously measured by detecting echo height voltage values of an ultrasonic response waveform using the ultrasonic probes 7, first, differences between adjacent thickness values when the entire vessel is measured with predetermined pitches are calculated, and a statistical distribution in the entire vessel is created.

Figure 33:
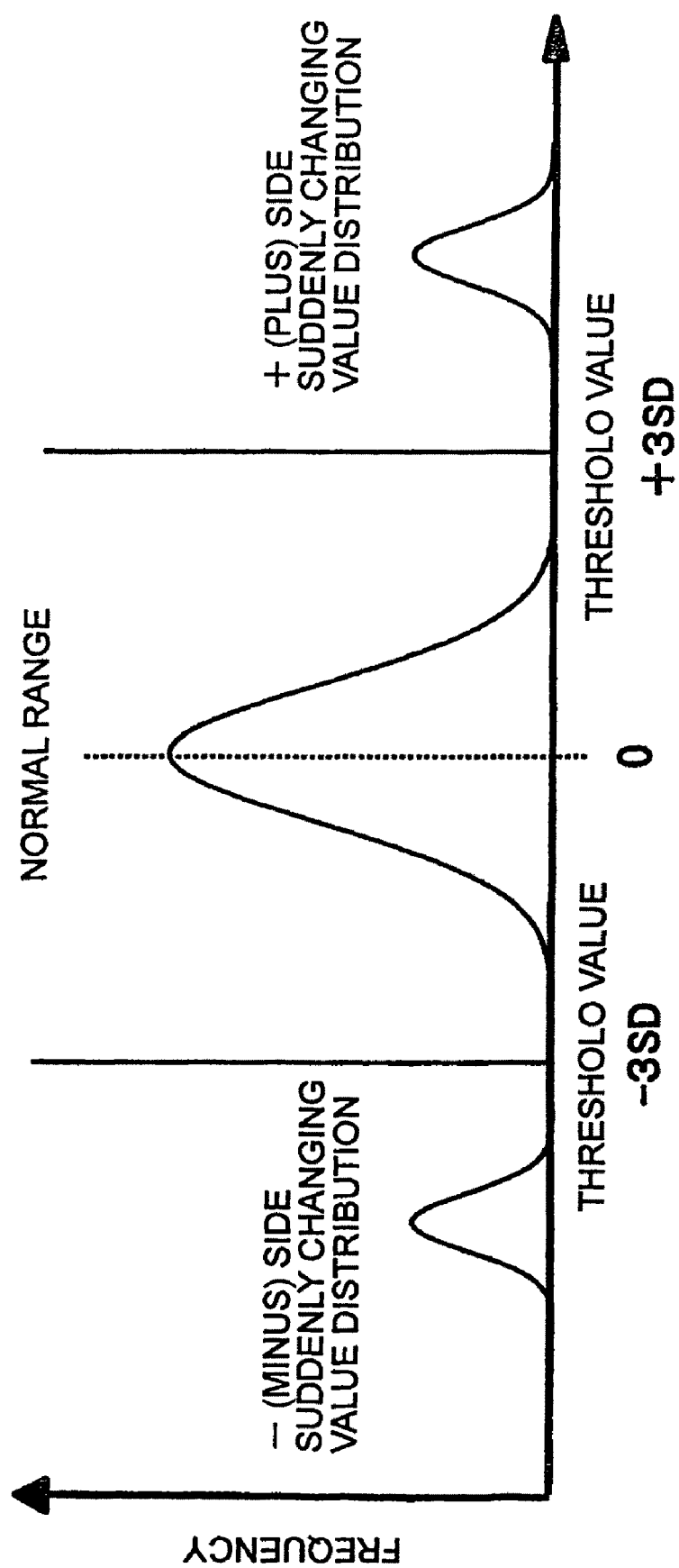
FIG. 33 shows a state in which, as a result of creating a statistical distribution in the entire vessel by calculating differences between adjacent thickness values when the entire vessel is measured with predetermined pitches, a standard difference distribution aggregates in a normal difference distribution with the average value "0" and suddenly changing value distributions are distributed separately at the − (minus) side and + (plus) side in the case where there is a lamination or inclusion in the vessel steel plate.

FIG. 33 shows an example of a normal difference distribution with the average value "0" as a center thereof and suddenly changing value distributions distributed separately at the – (minus) side and + (plus) side when there is a lamination or inclusion in the steel material of the vessel steel plate as a result of creating a statistical distribution in the entire vessel by calculating differences between adjacent thickness values when the entire vessel is measured with predetermined pitches.

Then, from the statistical distribution shown in FIG. 33, with the portion where the difference between thickness values becomes smaller than the normal range at the − (minus) side as a starting time point of a noise group, and further, with the portion where the difference between thickness values becomes larger than the normal range at the + (plus) side as an ending point of a noise group, a range including a pair of parts close to the starting time point and ending point of the noise groups with continuously small thicknesses therebetween are determined as a noise group.

Figure 31:
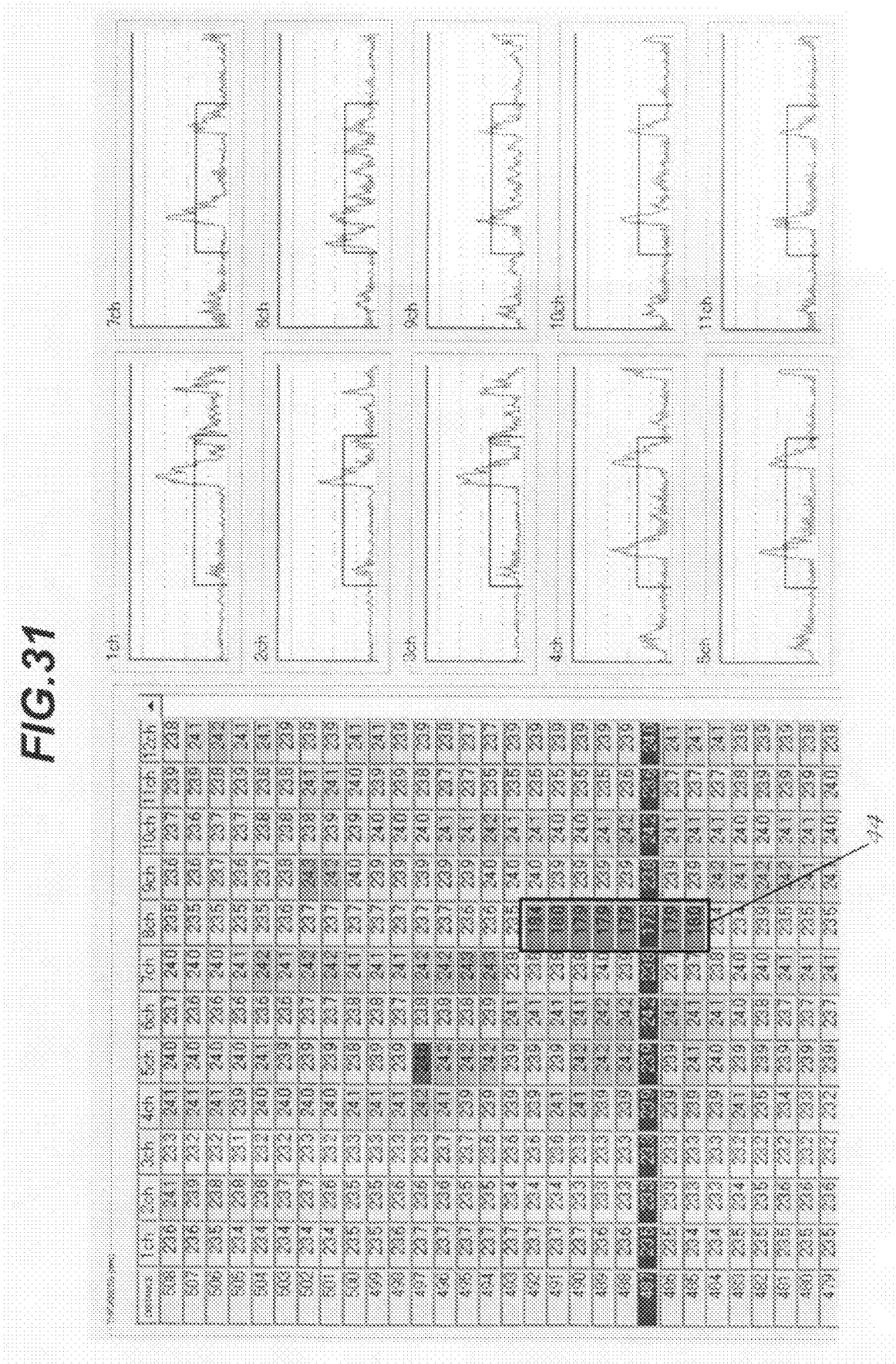
FIG. 31 is an explanatory diagram of a state in which, in the case where differences between adjacent thickness values when the entire vessel is measured with predetermined pitches with a portion where the difference between thickness values becomes smaller than the normal range at the − (minus) side as a starting time point of a noise group, and further, with a portion where the difference between thickness values becomes larger than the normal range at the + (plus) side as an ending point of a noise group, a range including a pair of parts close to the starting time point and ending point of the noise groups with continuously small thicknesses therebetween are determined as a noise group.

FIG. 31 is an explanatory diagram of a state in which, in the case where differences between adjacent thickness values when the entire vessel is measured with predetermined pitches with predetermined pitches with the portion where the difference between thickness values becomes smaller than the normal range at the − (minus) side as a starting time point of a noise group, and further, with the portion where the difference between thickness values becomes larger than the normal range at the + (plus) side as an ending point of a noise group, a range including a pair of parts close to the starting time point and ending point of noise groups with continuously small thicknesses therebetween are determined as a noise group. A thickness value 44 of thin thickness measured by the multiple echo waveform 43c detected by the ultrasonic probes 7 of 8ch shown in FIG. 31 can be determined as a noise group with a lamination or inclusion existing in the steel material of the vessel steel plate.

Further, since thickness is not displayed by designating the noise groups of the separation distributions dichotomized from the respective statistical distributions, erroneous display showing thinner thicknesses than real thicknesses due to separation between the vessel steel plate the surface layer can be prevented.

Next, using FIGS. 34 to 36, a method, after the thicknesses of the vessel steel plate are continuously measured by detecting echo height voltage values of an ultrasonic response waveform using the ultrasonic probes 7 from inside of the vessel provided with the jacket steel material on the outer circumferential part, of designating portions to be repaired from the outer side of the jacket steel material 4 will be described.

Figure 34:
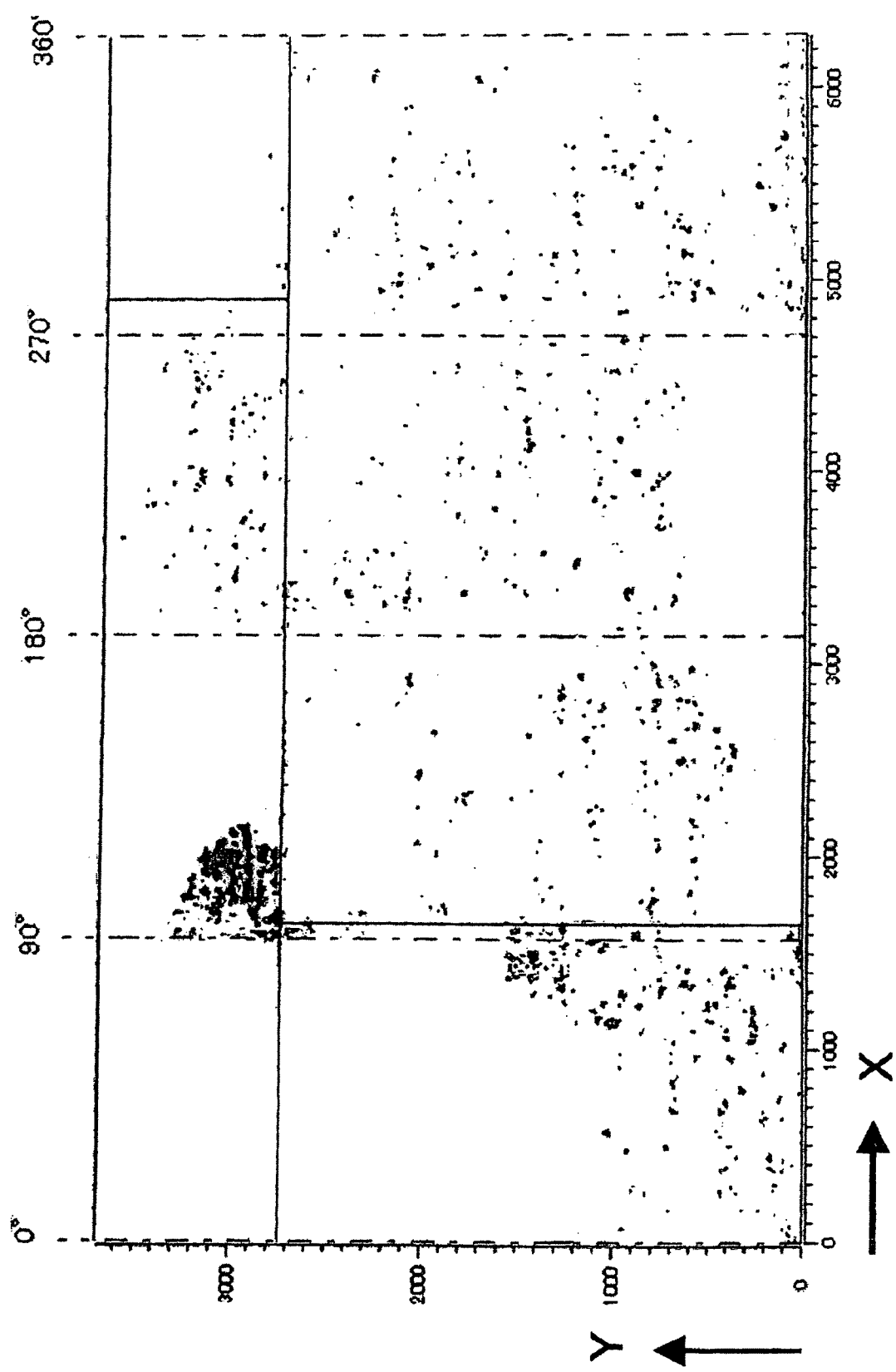
FIG. 34 shows a state in which measured thicknesses of the steel plate are plotted on two-dimensional coordinates for developing the inner surface side of the vessel barrel part substantially in a cylindrical form.

First, as shown in FIG. 34, the inner surface of the vessel barrel part 1b substantially in a cylindrical form is developed on (X,Y) two-dimensional coordinates, the thicknesses of the steel plate of the vessel barrel part 1b that have been continuously measured by the ultrasonic probes 7 mounted on the traveling carriage 5 are plotted.

Figure 36:
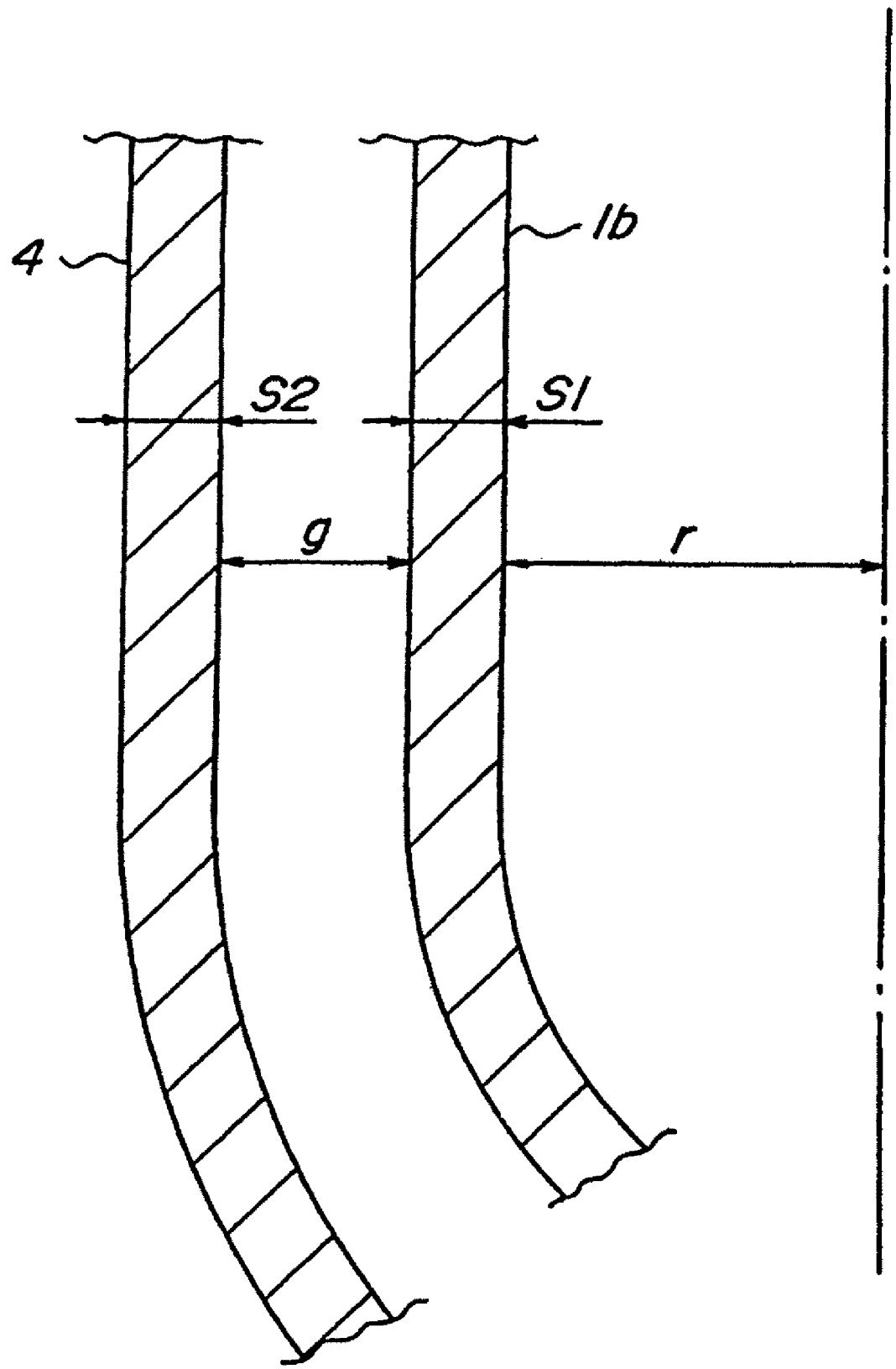
FIG. 36 is an explanatory diagram of a principle, assuming that the inner diameter of the vessel barrel part is r, the thickness of the vessel barrel part is S1, the spaced distance between the outer surface of the vessel barrel part and the inner surface of the jacket steel material is g, the thickness of the jacket steel material is S2, of performing (r+S1+g+S2)/r times magnifying coordinate transformation in the left and right directions with respect to the two-dimensional coordinates shown in FIG. 34.

Here, the respective parts in the developed view seen from the inner surface side of the vessel barrel part 1b and the respective parts in the developed view seen from the outer surface side of the vessel barrel part 1b are symmetrical, and further, as shown in FIG. 36, assuming that the inner diameter of the vessel barrel part 1b is r, the thickness of the vessel barrel part 1b is S1, the spaced distance between the outer surface of the vessel barrel part 1b and the inner surface of the jacket steel material 4 is g, the thickness of the jacket steel material 4 is S2, the inner circumference length of the vessel barrel part 1b is $2\pi r$, and the outer circumference length of the jacket steel material 4 is $2\pi(r+S1+g+S2)$. Accordingly, dimensions of the respective parts in the developed view seen from the inner surface side of the vessel barrel part 1b and dimensions of the respective parts in the developed view seen from the outer surface side of the vessel barrel part 1b are $(r+S1+g+S2)/r$ times magnified in the left and right directions.

Therefore, with respect to the two-dimensional coordinates of (X,Y) for developing the inner surface side of the vessel barrel part 1b and plotting the thicknesses of the steel plate of the vessel barrel part 1b that have been continuously measured by the ultrasonic probes 7 from the inner surface side of the vessel barrel part 1b, symmetrical coordinate transformation and $(r+S1+g+S2)/r$ times magnifying coordinate transformation in the left and right directions are simultaneously performed.

In such a case where symmetrical coordinate transformation and $(r+S1+g+S2)/r$ times magnifying coordinate transformation in the left and right directions are simultaneously performed on the (X,Y) two-dimensional coordinates, the coordinate transformation can be performed using the following transformation formula.

$$\begin{pmatrix} X' \\ Y' \end{pmatrix} = \begin{pmatrix} -(r+S1+g+S2)/r & , & 0 \\ 0 & & .1 \end{pmatrix} \begin{pmatrix} X \\ Y \end{pmatrix}$$

Figure 35:
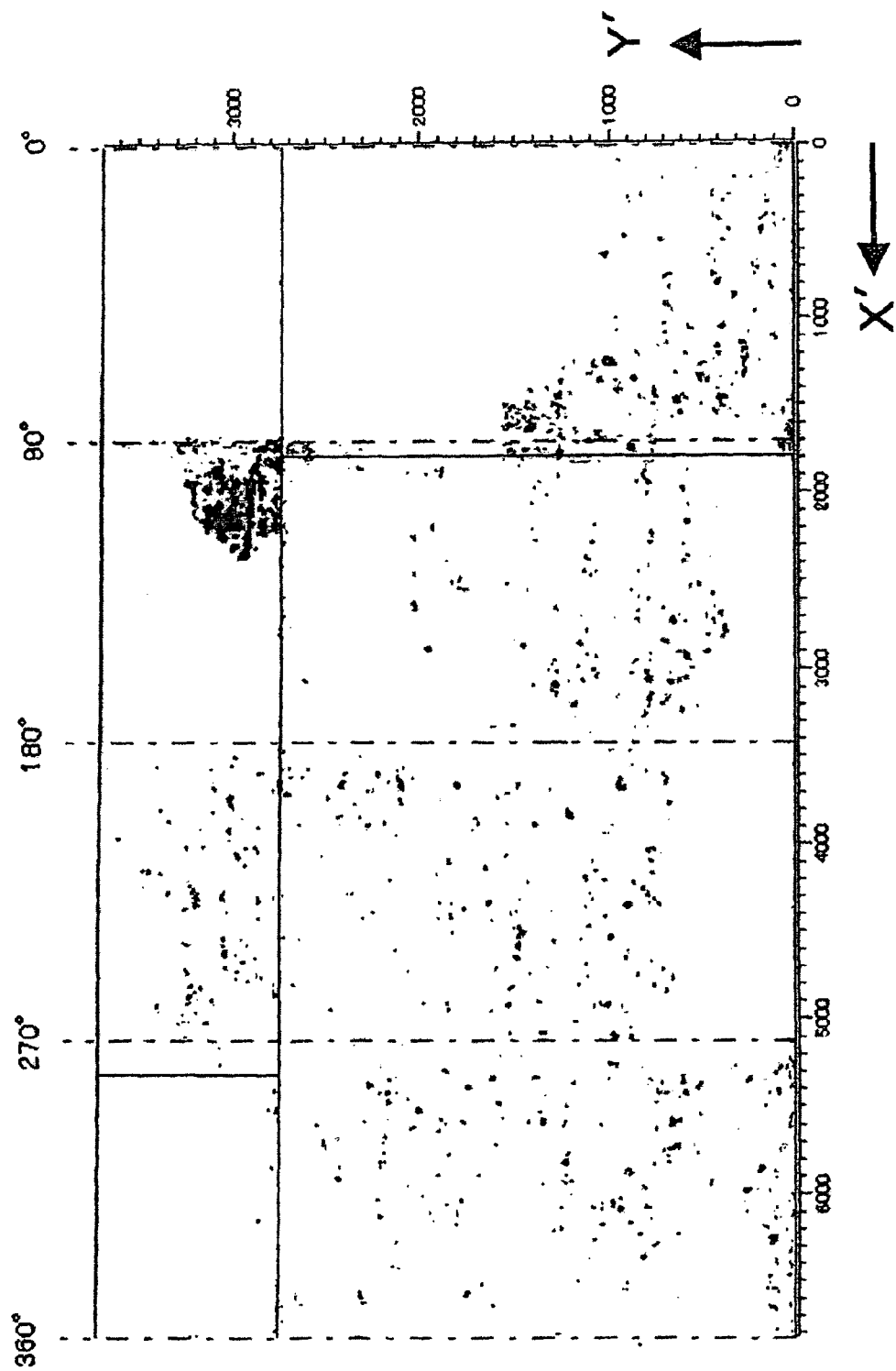
FIG. 35 shows a state in which symmetrical coordinate transformation and magnifying coordinate transformation in the left and right directions are simultaneously performed with respect to the two-dimensional coordinates shown in FIG. 34 on which the measured thicknesses of the steel plate are plotted.

Thus coordinate transformed (X',Y') two-dimensional coordinates are created as two-dimensional coordinates formed by developing the outer surface of the jacket steel material 4 as shown in FIG. 35.

The (X,Y) two-dimensional coordinates shown in FIG. 34 are displayed with the lower left point as an origin, the rightward direction of the X-axis as the plus direction, and the leftward direction of the Y-axis as the minus direction. The (X,Y) two-dimensional coordinates shown in FIG. 35 are displayed with the lower right point as an origin, the leftward direction of the X-axis as the plus direction, and the rightward direction of the Y-axis as the minus direction.

Then, as shown in FIG. 35, the portions to be repaired can be accurately designated from the outer side of the jacket steel material 4 based on the thickness of the vessel steel plate plotted on the (X',Y') two-dimensional coordinates.

Thus, the portions to be repaired can be accurately designated from the outer side of the jacket steel material 4 in a pinpoint narrow range, and repairing work of the vessel barrel part 1b can be conducted more efficiently compared to the conventional empirical repairing method.

The invention claimed is:

1. A device for measuring a thickness of a vessel steel plate comprising:
   a traveling carriage traveling with left and right front wheels and left and right rear wheels, and provided with a steering mechanism capable of changing a radius of curvature of a traveling track of the front wheels, the traveling carriage traveling on a steel plate of a vessel mirror part formed by a curved surface having a predetermined curvature and a circular projection form;
   an ultrasonic probe unit mounted on the traveling carriage and provided with a plurality of ultrasonic probes;
   a supporting point member detachable from a supporting point set at a central axis of the vessel mirror part; and
   a turning radius regulating member having one end to which the traveling carriage is connected rotatively via a rotation guide joint and the other end provided relative to the supporting point member rotatively around the supporting point member, and regulating a spaced distance between the supporting point set at the central axis of the vessel mirror part and the traveling carriage.

2. A device for measuring a thickness of a vessel steel plate comprising:
   a traveling carriage traveling with left and right front wheels and left and right rear wheels and provided with a magnetic material mounted thereon for exerting an attraction force on the vessel steel plate, the traveling carriage having a traveling driving mechanism that can drive the left and right rear wheels forward or backward independently and capable of traveling on a steel plate of a vessel barrel part substantially in a cylindrical form that continues in a direction substantially perpendicular to the vessel barrel part;

an ultrasonic probe unit on which a plurality of ultrasonic probes are mounted;

a carriage member movable relative to the traveling carriage in a direction crossed to a traveling direction of the traveling carriage, the ultrasonic probe unit having the plurality of ultrasonic probes being mounted on the carriage member; and obstruction detecting means for detecting obstructions in the traveling direction of the traveling carriage, wherein the thickness of the vessel steel plate is measurable by the ultrasonic probes in a state where the carriage member on which the ultrasonic probe unit is mounted is moved relative to the traveling carriage in a direction crossed to a traveling direction of the traveling carriage.

* * * * *